United States Patent
Ripplinger et al.

(10) Patent No.: US 8,674,122 B2
(45) Date of Patent: Mar. 18, 2014

(54) PROCESS FOR PREPARING DIVINYLARENE DIOXIDES

(75) Inventors: Eric B. Ripplinger, Lake Jackson, TX (US); David Jean, Friendswood, TX (US); David L. Burow, Taylor, TX (US); Khiet T. Pham, Lake Jackson, TX (US); Gyongyi Gulyas, Lake Jackson, TX (US); Bruce D. Hook, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/513,313

(22) PCT Filed: Dec. 17, 2010

(86) PCT No.: PCT/US2010/061019
§ 371 (c)(1),
(2), (4) Date: Jun. 1, 2012

(87) PCT Pub. No.: WO2011/084687
PCT Pub. Date: Jul. 14, 2011

(65) Prior Publication Data
US 2012/0253055 A1  Oct. 4, 2012

Related U.S. Application Data

(60) Provisional application No. 61/288,511, filed on Dec. 21, 2009.

(51) Int. Cl.
*C07D 301/03* (2006.01)
*C07D 301/12* (2006.01)

(52) U.S. Cl.
USPC .......................................... 549/531; 549/523

(58) Field of Classification Search
USPC ................................................. 549/523, 531
See application file for complete search history.

(56) References Cited

U.S. PATENT DOCUMENTS

| | | | |
|---|---|---|---|
| 2,388,235 A | 11/1945 | Bowman et al. |
| 2,591,573 A | 4/1952 | McBurney |
| 2,977,374 A | 3/1961 | Phillips et al. |
| 3,053,856 A | 9/1962 | Payne et al. |

OTHER PUBLICATIONS

Kologrivova et al., Maslozhirovaya Promyshlennost, (1978), vol. 11, pp. 37-38.
K. Kaneda et al., Chem Commun., 1998, pp. 295-296.
M. Worzakowska, (2007) vol. 103, pp. 462-469, Journal of Applied Polymer Science, John Wiley and Sons Inc. New York, US, No. 1.
Beller et al., Chemical Communications, (2009), p. 4883.

*Primary Examiner* — Taylor Victor Oh

(57) ABSTRACT

A process for preparing a divinylarene dioxide including reacting (a) at least one divinylarene; (b) at least one peroxycarboximidic acid; (c) at least one solvent; and (d) at least one basic compound, under conditions to form a reaction mixture containing a divinylarene dioxide product; and then separating the divinylarene dioxide product from the other reaction mixture components to obtain a purified divinylarene dioxide product.

20 Claims, 2 Drawing Sheets

PROCESS FOR PREPARING DIVINYLARENE DIOXIDES

CROSS REFERENCE TO RELATED APPLICATIONS

This is a §371 application of PCT International Patent Application Number PCT/US2010/061019 filed Dec. 17, 2010, and claims priority from provisional application Ser. No. 61/288,511, filed Dec. 21, 2009, which is incorporated herein by reference in its entirety.

BACKGROUND OF THE INVENTION

1. Field of the Invention

The present invention is related to a process for preparing divinylarene dioxides, particularly divinylarene dioxides derived from divinylbenzene. More specifically, the present invention relates to a process for preparing a divinylarene dioxide including reacting (a) at least one divinylarene; and (b) at least one peroxycarboximidic acid.

2. Description of Background and Related Art

In general, epoxidation of olefins can be accomplished by a variety of different methods. For instance, the prior art methods include: (1) reaction of an olefin with hypochlorite to form a chlorohydrin, followed by reaction with a base to form an epoxide; (2) oxidation by peroxy carboxylic acids; (3) oxidation by organic hydroperoxides with a catalyst; (4) oxidation by hydrogen peroxide with a catalyst; or (5) oxidation by other oxidants such as sodium hypochlorite, iodosyl benzene, or peroxycarbonate in the presence of a catalyst.

Epoxidation of olefins by peroxycarboximidic acids is disclosed in U.S. Pat. No. 3,053,856. In the process of U.S. Pat. No. 3,053,856, hydrogen peroxide reacts with a nitrile under controlled pH conditions to form a peroxycarboximidic acid which reacts with an olefin to form an epoxide and an amide. The overall reaction is shown below with acetonitrile and hydrogen peroxide used to make the peroxyacetimidic acid:

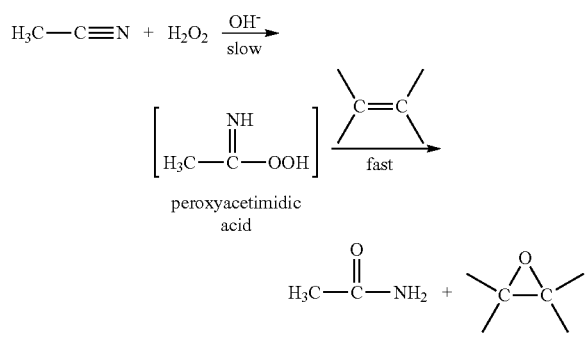

M. Worzakowska, *J. Appl. Poly. Sci.*(2007) vol103, pp462-469, discloses epoxidizing divinylbenzene (DVB) by a method similar to that described in U.S. Pat. No. 3,053,856 using acetonitrile-hydrogen peroxide with magnesium oxide catalyst and greater than a 4-fold molar excess of hydrogen peroxide to olefin. Worzakowska reports a 90 percent (%) degree of epoxidation. In the method of Worzakowska, DVB, acetonitrile, water (pH 10), and MgO are charged into a reactor, warmed to 50° C., whereupon addition of a mixture of 60% hydrogen peroxide and methanol are added slowly over 2 hours, followed by continued heating and stirring for a total of 5 hours. The method used by Worzakowska is disadvantaged in terms of process safety and economics due to the large excess of hydrogen peroxide required. This excess of hydrogen peroxide has to be recovered and reused for Worzakowska's method to be viable on an industrial scale.

U.S. Pat. No. 2,977,374 discloses epoxidizing DVB using peracetic acid in ethyl acetate and reports a divinylbenzene dioxide (DVBDO) yield of 49%. In U.S. Pat. No. 2,977,374, an 81% yield of styrene oxide is reported. Although olefins such as styrene and DVB are structurally similar, epoxidation of these two olefins will not give comparable results, as shown in U.S. Pat. No.2,977,374. Epoxidation using peracetic acid generates acetic acid as a co-product which is known to react with the epoxide product to give a hydroxy ester byproduct, thereby lowering the yield of the epoxide product. In the case of a diolefin, there is twice as great a probability that any given molecule of starting diolefin will form a byproduct as compared to the corresponding monoolefin.

In view of the problems with the known prior art processes, it is desired to provide a process to make a divinylarene dioxide such as DVBDO on an industrial scale which gives good yields of divinylarene dioxide product at the lowest possible oxidant cost.

SUMMARY OF THE INVENTION

The present invention is directed to a process for preparing divinylarene dioxides, particularly divinylarene dioxides derived from divinylbenzene, including reacting (a) at least one divinylarene; and (b) at least one peroxycarboximidic acid epoxidizing agent. In one embodiment, the reaction of the present invention includes conducting the reaction in the presence of at least one reaction solvent and at least one basic compound, under conditions to form a divinylarene dioxide product. In another embodiment, the reaction may be carried out such that the reaction mixture may be generally at a pH of about 7 or greater. In yet another embodiment, the peroxycarboximidic acid used in the present invention may be (i) a pre-formed peroxycarboximidic acid, (ii) a peroxycarboximidic acid formed in situ in the reaction mixture, or (iii) a combination of (i) and (ii). In other embodiments, the reaction may be carried out such that the mole ratio of peroxycarboximidic acid to ethylenic double bonds of the divinylarene comprises, for example, less than about 2.0; wherein the yield of divinylarene monoxide based on divinylarene comprises, for example, less than about 20%; and/or wherein the yield of divinylarene dioxide based on divinylarene comprises, for example, greater than about 60%.

In yet another embodiment of the present invention, the peroxycarboximidic acid may be formed in situ in the reaction mixture by adding aqueous hydrogen peroxide to a mixture of the divinylarene being epoxidized, a nitrile, a reaction solvent, and a basic compound added to maintain the pH of the reaction mixture at, for example, greater than or equal to about 7; and wherein the reaction may be conducted at temperature of, for example, from about 40° C. to about 50° C.

In still another embodiment of the present invention, the peroxycarboximidic acid may be pre-formed by a separate reaction of a nitrile with an aqueous hydrogen peroxide, in the presence of a basic compound and optionally a reaction solvent; and then the pre-formed peroxycarboximidic acid may be fed, as the solution in which the peroxycarboximidic acid was made, to a mixture of the divinylarene being epoxidized, a reaction solvent, and a basic compound added to the epoxidation reaction mixture to maintain the pH greater than about 7.

BRIEF DESCRIPTION OF THE DRAWINGS

For the purpose of illustrating the present invention, the following drawings show a form of the present invention which is presently preferred. However, it should be understood that the present invention is not limited to the precise arrangements and apparatuses shown in the drawings. In the accompanying drawings, like reference numerals are used to denote like parts throughout the several drawings.

DETAILED DESCRIPTION OF THE INVENTION

Figure 1:
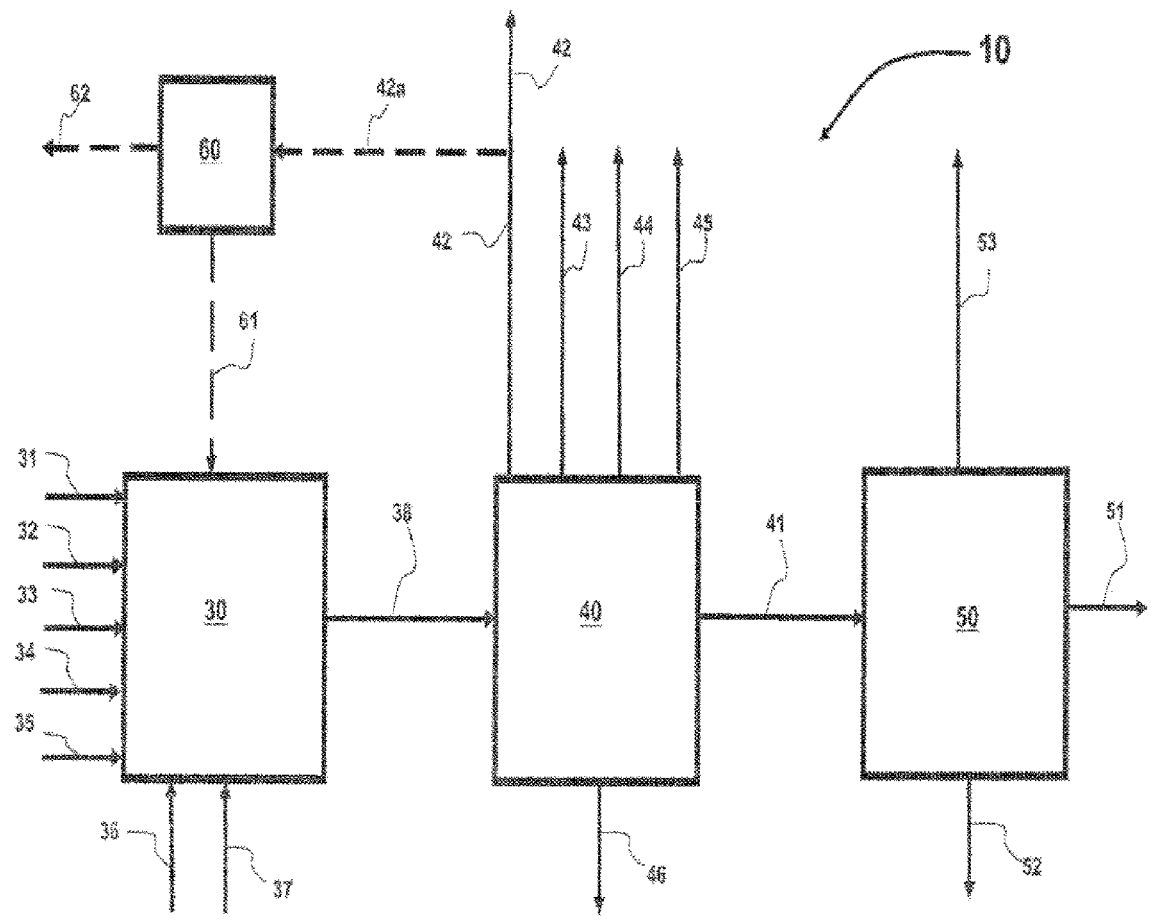
FIG. 1 is a block flow diagram showing one embodiment of the process of the present invention.

In accordance with the present invention, the epoxidation of divinylarene compounds to obtain divinylarene dioxide compounds may be carried out with a peroxycarboximidic acid. The source of divinylarene useful in the present invention may come from any known sources and particular to known processes for the preparation of divinylarenes. For example, divinylarenes can be prepared with salt or metal wastes from arenes and ethylene.

The divinylarene reactant useful in the process of the present invention may be illustrated by general chemical Structures I-IV as follows:

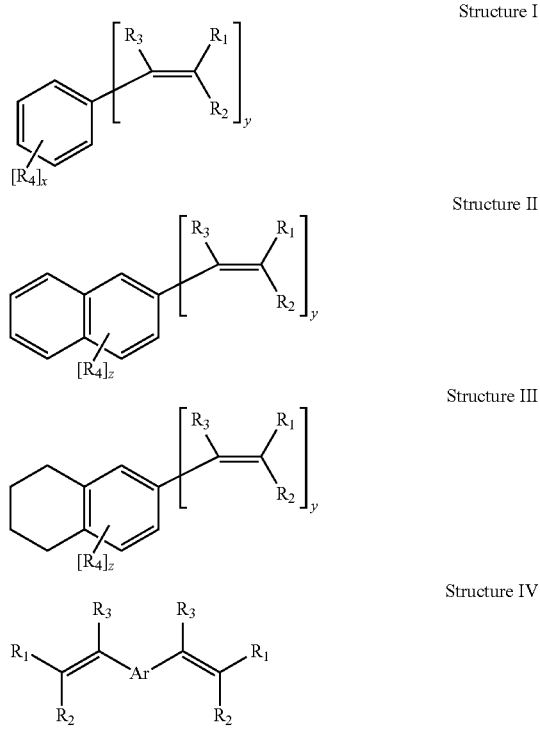

Structure I

Structure II

Structure III

Structure IV

In the above Structures I, II, III and IV of the divinylarene reactant of the present invention, each $R_1$, $R_2$, $R_3$ and $R_4$ individually may be hydrogen; an alkyl, cycloalkyl, an aryl or an aralkyl group, wherein the alkyl, cycloalkyl, aryl, and aralkyl groups may have from 1 to about 18 carbon atoms and preferably from 1 to 4 carbon atoms; or an oxidant-resistant group including for example a halogen, a nitro, an isocyanate, or an R'O group, wherein R' may be an alkyl, an aryl or an aralkyl group each individually having from 1 to about 18 carbon atoms and preferably from 1 to 4 carbon atoms; x may be an integer of 0 to 4; y may be an integer greater than or equal to 2; x+y may be an integer less than or equal to 6; z may be an integer of 0 to 6; z+y may be an integer less than or equal to 8; and Ar is an arene fragment including for example, 1,3-phenylene group.

In one embodiment of the present invention, the divinylarene useful in the present invention may comprise any substituted or unsubstituted arene nucleus bearing two vinyl (also referred to herein as "C=C bonds", "olefinic" or "ethylenic double bonds") groups in any ring position. The arene may include for example benzene, substituted benzenes, or (substituted) ring-annulated benzenes, and mixtures thereof. In one embodiment, divinylbenzene may be ortho, meta, or para isomers or any mixture thereof. Additional substituents may consist of oxidation-resistant groups including for example a saturated alkyl, or an aryl, wherein the saturated alkyl may have from 1 to about 18 carbon atoms and preferably from 1 to 4 carbon atoms, and wherein the aryl may have from 4 to about 18 carbon atoms and preferably from 6 to 10 carbon atoms; a halogen; a nitro, an isocyanate; or a R'O-wherein R' may be a saturated alkyl, an aryl, or an aralkyl each individually having from 1 to about 18 carbon atoms and preferably from 1 to 4 carbon atoms; or mixtures thereof. Ring-annulated benzenes may include for example naphthlalene, tetrahydronaphthalene, and the like, and mixtures thereof.

In another embodiment, the divinylarene may contain quantities of substituted arenes. The amount and structure of the substituted arenes depend on the process used in the preparation of the divinylarene. For example, DVB prepared by the dehydrogenation of diethylbenzene (DEB) may optionally contain quantities of ethylvinylbenzene (EVB), naphthalene, polyethylbenzenes (e.g. diethylbenzene, triethylbenzene, tetraethylbenzene, pentaethylbenzene, diphenylethane, other aklylated benzenes, and higher molecular weight oils), free radical inhibitors, or mixtures thereof.

In one embodiment of the present invention, DVB may be epoxidized wherein DVB may optionally contain EVB. The DVB used can be a high purity DVB to make DVBDO with a very low amount of ethylvinylbenzene oxide (EVBO)."High purity" with reference to DVB herein means, for example, a DVB which contains greater than about 80% DVB in one embodiment, greater than about 90% DVB in another embodiment, and greater than about 95% DVB in yet another embodiment with the remainder being impurities or other compounds such as EVB.

In another embodiment, the process may provide, as a co-product, one or more divinylarene monoxides, alkyl-vinyl-arene monoxides, or mixtures thereof. When a monoxide product is produced as a co-product, the monoxide may be purified such that the purified monoxide product may have a purity of greater than about 50% in one embodiment, greater than about 80% in another embodiment, and greater than about 90% in yet another embodiment.

The divinylarene used in the process of the present invention may include for example divinylbenzene, divinylnaphthalene, divinylbiphenyl, divinyldiphenylether; or mixtures thereof. In one preferred embodiment, the present invention uses divinylbenzene as the divinylarene reactant. In the embodiment using divinylbenzene as the divinylarene reactant, the divinylarene dioxide formed comprises divinylbenzene dioxide.

As aforementioned, the peroxycarboximidic acid reactant used in the present invention may be (i) pre-formed, (ii) formed in situ in the reaction mixture, or (iii) a combination of (i) and (ii). The peroxycarboximidic acid useful in the present invention may include for example a peroxycarboximidic acid reactant with the general chemical formula as follows:

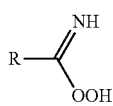

In the above structure for the peroxycarboximidic acid epoxidizing agent being employed, R may be a saturated hydrocarbon having from 1 to about 18 carbon atoms, preferably from 1 to about 12 carbon atoms, and more preferably from 1 to about 8 carbon atoms; or R may be an aromatic hydrocarbon having from 1 to about 18 carbon atoms, preferably from 1 to about 12 carbon atoms, and more preferably from 1 to about 8 carbon atoms; and wherein R is free of non-aromatic multiple bonds.

Examples of peroxycarboximidic acids useful in the present invention include, but are not limited to, peroxypropionimidic acid; peroxycapronimidic acid; peroxycaprinimidic acid; peroxytridecaneimidic acid; peroxy 1- and 4-methycyclohexanecarboximidic acid; peroxycyclohexaneacetimidic acid; or mixtures thereof.

In one embodiment of the process of the present invention, the epoxidation reaction can be represented by the following reaction Scheme I:

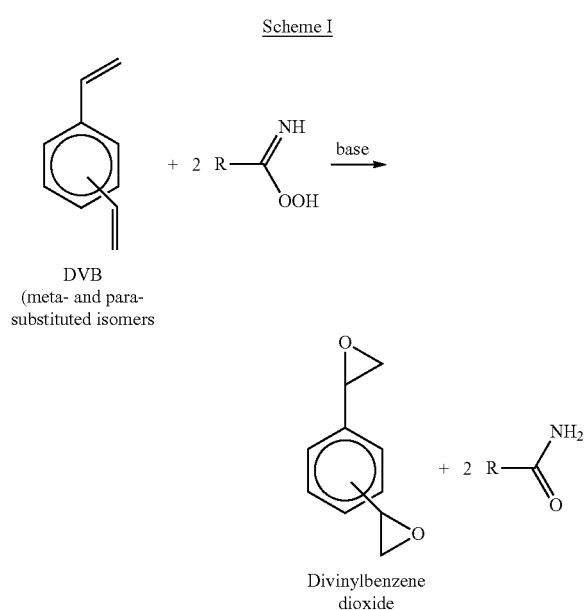

The above example, Scheme I, shows the epoxidation process of the present invention wherein divinylbenzene (DVB) is epoxidized with a peroxycarboximidic acid having the general formula:

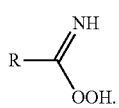

wherein R may be the same as defined above.

As aforementioned, the peroxycarboximidic acid epoxidizing agents of the present invention can be obtained in various ways such as for example by pre-forming the peroxycarboximidic acid in a separate and independent reaction; or in situ in the reaction mixture. While separately pre-formed peroxycarboximidic acid can be successfully used in the reaction, the peroxycarboximidic acid epoxidizing agent is advantageously formed in situ in the reaction mixture. The peroxycarboximidic acid can be formed in situ in the reaction mixture for example by reacting a nitrile with hydrogen peroxide.

The present invention makes use of an in situ technique in carrying out the epoxidation by adding a nitrile and hydrogen peroxide ($H_2O_2$) to the divinylarene to be epoxidized, the peroxycarboximidic acid being formed from the nitrile and $H_2O_2$ under slightly basic conditions (e.g., pH of at least greater than or equal to($>$) about 7 as measured by a pH meter) and simultaneously epoxidizing the divinylarene compound to form a divinylarene dioxide and an amide as products. In order to maintain the pH at ≥about 7, a base may be added to the reaction mixture.

The nitrile compound employed in making the peroxycarboximidic acid in situ may be a compound in which the nitrile group is the only group capable of reacting with hydrogen peroxide. Especially useful nitriles may be those having the following formula:

wherein R in the above structure may be the same as defined above.

Nitriles in which the nitrile group is directly linked to an aromatic ring may be especially useful since these are known to form peroxycarboximidic acids which may be more active than the saturated nitriles and thus permit epoxidation in a shorter time, giving increased plant capacity.

Representative examples of nitriles used in the present invention, which on reaction with hydrogen peroxide, may be advantageously used to make carboximidic acids for use as the epoxidizing agents of the present invention, include one or more of the following examples: aliphatic nitriles such as acetonitrile resulting in peroxyacetimidic acid with the following chemical structure:

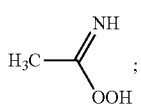

propionitrile resulting in peroxypropionimidic acid; capronitrile resulting in peroxycapronimidic acid; caprinitrile resulting in peroxycaprinimidic acid; tridecanenitrile resulting in peroxytridecaneimidic acid; cycloaliphatic nitriles such as 1- and 4-methylcyclohexanenitriles resulting in peroxy 1- and 4-methycyclohexanecarboximidic acids; cyclohexanenitrile resulting in peroxycyclohexaneacetimidic acid; aromatic nitriles such as ortho-, meta-, and para-tolunitriles, resulting in peroxyortho-, meta-, and para-toluimidic acids; benzonitrile resulting in peroxybenzimidic acid with the following structure:

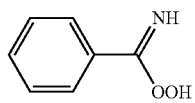

wherein the above peroxybenzimidic acid may be especially active as an epoxidizing agent; or mixtures thereof.

Beta-hydroxynitriles readily obtained by reacting hydrogen cyanide with epoxy compounds may be another useful type of nitrile for use in the present invention. For example beta-hydroxypropionitrile which forms peroxybeta-hydroxypropionimidic acid by reaction with hydrogen peroxide can be used.

Polynitriles can also be used instead of mononitriles in making the peroxycarboximidic acids epoxidizing agents for use in the present invention. Polynitrile is defined as any molecule with two or more nitrile groups wherein the nitrile groups are separated by 1 to 18 carbon atoms between the nitrile groups. For example, dinitriles such as malononitrile, hexamethylene dicyanide, adiponitrile, and mixtures thereof can be used in the present invention. Soluble polyacrylonitriles may be another type of nitrile useful in the present invention.

In one preferred embodiment, the nitrile useful in the present invention may comprise acetonitrile, benzonitrile, propionitrile or mixtures thereof.

Especially useful peroxycarboximidic acids may be those having the following formula:

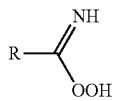

wherein R in the above structure may be the same as defined above.

In another embodiment, when the peroxycarboximidic acid is formed in situ in the reaction mixture for example by reacting a nitrile with hydrogen peroxide, the over-all reaction of the process of the present invention taking place can be represented by the following reaction Scheme II:

Scheme II

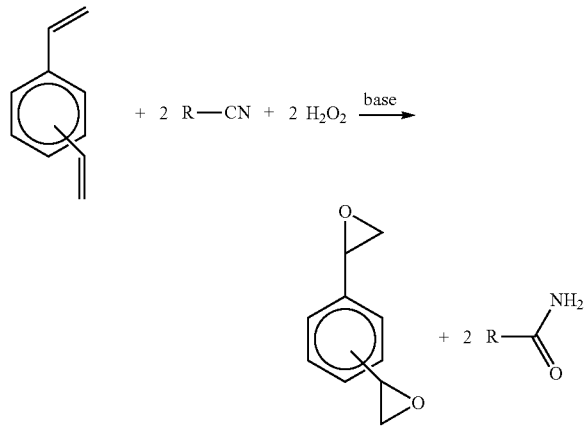

The above example, Scheme II shows an embodiment of the process of the present invention wherein divinylbenzene (DVB) is epoxidized and a peroxycarboximidic acid is formed in situ during the epoxidation. In Scheme II, R may be the same as defined above.

As aforementioned, the peroxycarboximidic acid can be prepared (pre-formed) prior to the use of such peroxycarboximidic acid in the reaction mixture by a separate reaction of a selected nitrile compound, such as for example any one or more of nitriles described above, with hydrogen peroxide. Then the pre-formed peroxycarboximidic acid may be added to the divinylarene compound to be epoxidized with intimate mixing under reaction conditions. It may not be necessary in such a case to isolate the peroxycarboximidic acid in order to use it for the epoxidation in the presence of the required base.

An alternate method of making pre-formed peroxycarboximidic acid epoxidizing agent for use in the reaction of the present invention may be for example by reacting an imido acid chloride such as one having the following structure:

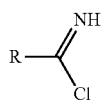

with a peroxide under basic conditions. In one embodiment, hydrogen peroxide, for instance, sodium hydroxide, sodium peroxide, sodium perborate, or the like, or mixtures thereof can be used alone or in combination with a base. R in the above structure may be the same as defined above.

Whether pre-formed or made in situ, at least one mole of the peroxycarboximidic acid per mole of epoxy group produced therewith may be generally used in the process of the present invention. However, different mole proportions of divinylarene compound to peroxycarboximidic acid epoxidizing agent can be employed. For example, it is often advantageous to employ a stoichiometric excess of one of the reactants in order to promote complete reaction of the other reactant at a faster rate. The divinylarene which is a component of the present invention contains two ethylenic double bonds. Generally, ratios of from about 0.25 mole to about 4 moles of peroxycarboximidic acid epoxidizing agent per mole of ethylenic double bond of the divinylarene may be used. In another embodiment of the process of the present invention, ratios of from about 0.75 mole to about 2 moles of peroxycarboximidic acid per mole of ethylenic double bond of the divinylarene may be used; and in yet another embodiment, ratios of from about 0.95 mole to about 1.30 mole of peroxycarboximidic acid per mole of ethylenic double bond of the divinylarene may be used.

In another embodiment, when the peroxycarboximidic acid is being formed in situ in the reaction mixture from a nitrile and hydrogen peroxide, generally ratios of from about 0.25 mole to about 4 moles of hydrogen peroxide per mole of ethylenic double bond of the divinylarene may be used. In still another embodiment of the process of the present invention, ratios of from about 0.75 mole to about 2 moles of hydrogen peroxide per mole of ethylenic double bond of the divinylarene may be used; ratios of from about 1.0 mole to about 2.0 moles of hydrogen peroxide per mole of ethylenic double bond of the divinylarene may be used in yet another embodiment; and ratios of from about 1.05 mole to about 1.30 mole of hydrogen peroxide per mole of ethylenic double bond of the divinylarene may be used in still another embodiment.

In order to illustrate one advantage of using the above stated ratios of hydrogen peroxide per mole of ethylenic double bond, a sequential epoxidation of both ethylenic double bonds of, for example, DVB with a peroxycarboximidic acid can be shown as Schemes III and IV which follow; said sequential epoxidation representing one embodiment of the process of the present invention:

Scheme III

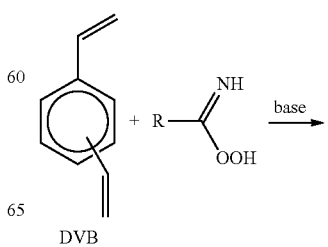

DVB

-continued

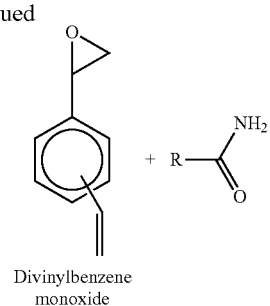

Divinylbenzene
monoxide

Scheme IV

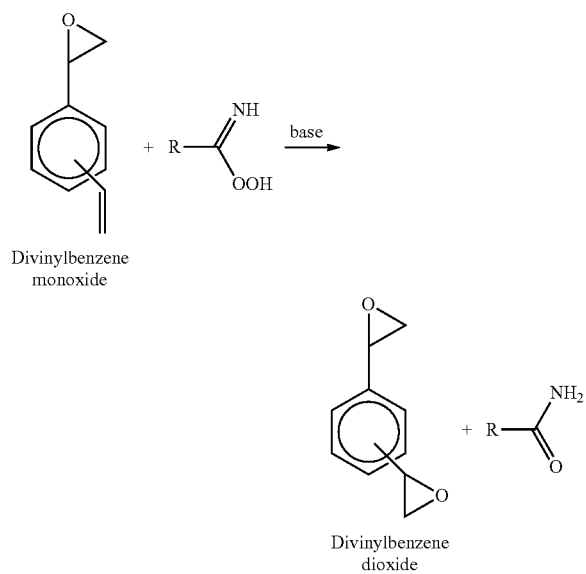

Divinylbenzene
monoxide

Divinylbenzene
dioxide

In the above example of the sequential epoxidation, illustrated by Schemes III and IV, divinylbenzene (DVB) is reacted with a peroxycarboximidic acid forming a divinylbenzene monoxide and an amide (Scheme III) followed by further reaction of the monoxide with a peroxycarboximidic acid forming a divinylbenzene dioxide and an amide (Scheme IV). In the above chemical structures of equations Schemes III and IV, R may be the same as defined above.

It has been found that if a high degree of reaction of ethylenic double bonds to epoxide groups is not obtained, then a substantial amount of divinylarene and/or divinylarene monoxide may remain in the reaction product. The above stated ratios of hydrogen peroxide to ethylenic double bond advantageously may give a high degree of reaction to the desired divinylarene dioxide.

Regardless of whether the peroxycarboximidic acid is (1) made in situ or (2) preformed, if a mole excess of ethylenic double bonds to hydrogen peroxide is used, then a large amount of divinylarene starting material and divinylarene monoxide may remain at the end of the epoxidation reaction; and separation of a significant amount of divinylarene and divinylarene monoxide from the divinylarene dioxide to obtain a pure product of divinylarene dioxide may be required. Therefore, it may be advantageous to use a slight mole excess of hydrogen peroxide relative to ethylenic double bonds in the process of the present invention, in order to obtain high conversion of ethylenic double bonds to epoxide groups while not using an undue excess of hydrogen peroxide, so that both desired embodiments, high conversion of ethylenic double bonds to epoxide groups and minimal use of hydrogen peroxide can be achieved.

An embodiment of the present invention includes for example a process for epoxidation of divinylarenes with a peroxycarboximidic acid, pre-formed or formed in situ, which uses a ratio of about 1.0 mole to about 2.0 moles of hydrogen peroxide per mole of ethylenic double bond, and more preferably a ratio of about 1.05 mole to about 1.30 mole of hydrogen peroxide per mole of ethylenic double bond, with the reaction conducted at the conditions described herein for the process of the present invention.

The process of the present invention advantageously provides one or more, and preferably all, of the following results:

(1) The conversion of charged divinylarene may comprise greater than about 80% conversion in one embodiment; greater than about 90% conversion in another embodiment; greater than about 98% conversion in yet another embodiment; and greater than about 99% conversion of charged divinylarene in still another embodiment. An objective of the present process is to obtain a 100% conversion of charged divinylarene, and generally the conversion of charged divinylarene may be from about 80% to about 100% conversion in one embodiment; from about 90% to about 100% conversion in another embodiment; from about 98% to about 100% conversion in yet another embodiment; and from about 99% to about 100% in still another embodiment.

(2) The percent yield of an intermediate divinylarene monoxide based on charged divinylarene may comprise less than about 50% in one embodiment; less than about 20% in another embodiment; less than about 10% in yet another embodiment; and less than about 5% in still another embodiment. In another embodiment, the percent yield of divinylarene monoxide based on divinylarene may comprise from about 0.1% to about 50% in one embodiment; from about 0.1% to about 20% in another embodiment; from about 0.1% to about 10% in yet another embodiment; from about 0.1% to about 5% in still another embodiment; and from about 0.1% to about 2% in yet another embodiment.

(3) The percent yield of divinylarene dioxide product based on divinylarene may comprise greater than about 50% yield in one embodiment; greater than about 60% yield in another embodiment; greater than about 70% yield in yet another embodiment; and greater than 80% yield of divinylarene dioxide in still another embodiment. An objective of the present process is to obtain a 100% yield of divinylarene dioxide product, and generally the percent yield of divinylarene dioxide product based on divinylarene may comprise from about 50% to about 100% yield of divinylarene dioxide; from about 60% to about 100% yield in another embodiment; from about 70% to about 100% yield in another embodiment; and from about 80% to about 100% yield in yet another embodiment.

(4) The percent yield of epoxide groups based on charged hydrogen peroxide may comprise greater than about 50% yield of epoxide groups in one embodiment; greater than about 60% yield in another embodiment; greater than about 70% yield of epoxide groups in another embodiment, and greater than about 90% in still another embodiment. An objective of the present process is to obtain a 100% yield of epoxide groups based on charged hydrogen peroxide, and generally the percent yield of epoxide groups may comprise from about 50% to about 100% yield; from about 60% to about 100% yield in another embodiment; from about 70% to about 100% yield in another embodiment; and from about 90% to about 100% yield in yet another embodiment.

In an embodiment wherein the peroxycarboximidic acid is being formed in situ in the reaction mixture from a nitrile, in general, mole ratios of nitrile to hydrogen peroxide of from about 0.5:1 to about 4:1 can be used in one embodiment; ratios of nitrile to hydrogen peroxide of from about 1:1 to about 3:1 can be used in another embodiment, and ratios of from about 1.2:1 to about 2.5:1 can be used in yet another embodiment. In such cases the ranges of hydrogen peroxide to ethylenic double bonds of the divinylarene may be in the range described above for the process of the present invention. When employing a polynitrile for in situ formation of the epoxidizing agent by reaction with hydrogen peroxide, mole proportions which take into account the number of nitrile groups per mole of the starting nitrile should be used.

The reaction may be preferably carried out in the liquid phase using a solvent wherein the solvent may include water and/or one or more organic solvents suitable for the reactants. For example, aqueous solutions of hydrogen peroxide and/or basic compounds may be used in the present invention. When epoxidizing divinylarene compounds have a low solubility in water and/or using peroxycarboximidic acids which are substantially water insoluble, an organic solvent for the reaction may be useful instead of, or together with, water. Alcohols, particularly water soluble alcohols, may be useful solvents, including methanol, ethanol, isopropanol, 1-methoxy-2-propanol, isobutyl alcohol, tert-butyl alcohol, or mixtures thereof. Polyhydric alcohols, for instance, ethylene glycol, 2-methyl-2,4-pentanediol, or mixtures thereof can be used. Hydrocarbon solvents, such as for example aromatic hydrocarbon solvents including toluene, benzene, xylenes, and the like; aliphatic hydrocarbon solvents including pentane, hexane, cyclohexane, and the like; or mixtures thereof, can be used in the present invention. Other non-acidic solvents can be used in the present invention such as ketones, ethers, chlorinated solvents, esters, or mixtures thereof. For example, the solvents useful in the present process may include acetone, methyl ethyl ketone, 4-methyl-2-pentanone, cyclohexanone, diacetone alcohol, dimethyl ether, ethylene glycol monomethyl ether, ethylene glycol monoacetate, ethyl acetate, dioxane, methylene chloride, chloroform, or mixtures thereof. Solvents which are free from polymerizable ethylenic linkages may also be used in the present invention process.

In one preferred embodiment, the reaction solvent may comprise for example, methanol, isopropanol, diethyl ether, benzene, toluene, ethyl acetate, 4-methyl-2-pentanone, 1-methoxy-2-propanol, or mixtures thereof.

Generally, when the reaction is carried out with amounts of liquid organic solvents, the weight ratio of the organic solvent to divinylarene may be less than about 20 in one embodiment, less than about 10 in another embodiment, and less than about 5 in yet another embodiment. In other embodiments of the present invention, the weight ratio of the organic solvent to divinylarene may be from about 0.1 to about 20, preferably from about 0.5 to about 10, and more preferably from about 1 to about 5.

Another embodiment of the present invention includes for example the use of the above described nitriles, both as a reactant and as a reaction solvent for the composition of the present invention. In this instance, an excess of nitrile can be used in order to provide both the needed reaction and the functionality of the nitrile to function as a solvent, wherein the excess of nitrile falls within the above discussed ranges of weight ratios.

The reaction mixture can be single phase or multiphase, that is, the reaction mixture can comprise a single homogeneous phase; or the reaction mixture can comprise more than one liquid and/or solid phases.

For maintaining the pH of the reaction mixture at a pH of greater than or equal to about 7, an organic or inorganic basic compound can be added to the reaction mixture. Both substantially soluble and substantially insoluble basic compounds may be effectively used in the present invention, provided that the basic compound maintains the required pH of the reaction mixture. Because basic inorganic compounds may be readily availability at low cost, basic inorganic compounds may be generally advantageous.

Suitable basic compounds useful in the present invention include for example, inorganic hydroxides, examples of which may be alkali and alkaline earth hydroxides such as sodium hydroxide, potassium hydroxide, ammonium hydroxide, magnesium hydroxide, calcium hydroxide, and the like, or mixtures thereof; the corresponding oxides of alkali and alkaline earth metals, for example, sodium oxide, calcium oxide, magnesium oxide, and the like, or mixtures thereof; and basic salts such as water-soluble carbonates, bicarbonates, phosphates and the like, or mixtures thereof, examples of which may be sodium carbonate, sodium bicarbonate, potassium bicarbonate, tripotassium phosphate, and the like; or mixtures thereof.

In one preferred embodiment, the basic compound may comprise a hydroxide, a bicarbonate, or mixtures thereof. In another embodiment, the basic compound may comprise an alkali metal hydroxide, an alkali metal bicarbonate, or mixtures thereof. In yet another embodiment, the basic compound may comprise sodium hydroxide, potassium hydroxide, sodium bicarbonate, potassium bicarbonate, or mixtures thereof.

Organic basic compounds used in the present invention, in general, may be less preferred because of their higher cost than inorganic bases. However, organic bases may still be useful in the present invention. Among the organic basic compounds which may be used in the present invention, include, for instance, salts of phenols such as potassium phenates, calcium phenates, sodium meta-methyl phenoxide, sodium naphthoxide; amines such as methylamine, dimethylamine, trimethylamine, and higher analogues such as triethylamine, tri-n-propylamine, tri-n-butylamine and the like; and mixtures thereof.

Aqueous solutions of any water-soluble basic compounds may be used in the composition; and can range generally from about 0.1 wt % to about 50 wt % in one embodiment; from about 1 wt % to about 40 wt % in another embodiment, and from about 4 wt % to about 10 wt % in yet another embodiment.

In some embodiments, there may be operating advantages in using an insoluble form of the basic compound. For example, anion exchange resins, especially amine or quaternary ammonium base resins may be a particularly convenient form of insoluble base for use in the process of the present invention. Examples of these suitable base resins may include, for instance, the amination products of chloromethylated styrene-divinylbenzene copolymers described in U.S. Pat. No. 2,591,573, incorporated herein by reference; resins made by the process of U.S. Pat. No. 2,388,235, incorporated herein by reference; anion resins; and weak base ion exchange resins; and the like, or mixtures thereof. The base resins may be used in the free base form or in the form of the salts, for instance, the carbonate salts of the strong base resins. Another class of insoluble basic compounds useful in the present invention may include for example hydrotalcites, which are synthetic anionic clays with Brucite-like layers having positive charge with anionic species in the interlayer, for example the hydrotalcite $Mg_{10}Al_2(OH)_{24}CO_3$ described in K. Kaneda et al., Chem. Commun., 1998, pp. 295-296 and prepared by the references cited therein; incorporated herein by reference.

The rate of the present invention reaction is pH dependent, and a pH of at least greater than or equal to about 7, and in another embodiment, greater than about 9 may be desired in order to promote rapid reaction. Generally, the pH of the reaction mixture may comprise a pH of between greater than about 7 up to about 12.1 In one embodiment, the basic compound is used to maintain the pH of the reaction mixture at from about 9 to about 11.5.1 In another embodiment, beneficial results may be obtained when the addition of the basic compound is controlled so as to maintain the pH of the reaction mixture in the range of from about 9 to about 10.5.1 In yet another embodiment, the pH of the reaction may be maintained in the range of about 9.5 to about 10.5.1 In still another embodiment, the pH of the reaction is maintained in the range of about 9.5 to about 10.1.1 The term "pH" as referred to herein means the pH as measured in the reaction solution at the reaction temperature by a pH meter equipped with a Thermoscientific #8272BN pH probe, which may be calibrated using standard pH 7 and pH 10 buffers obtained from Fisher Scientific. A basic compound addition profile with one or more constant addition rates, or intermittent additions, may be used as an alternative system to pH control. The basic compound may be for example sodium hydroxide (NaOH).

Whether pH control or a NaOH addition profile is used, the total NaOH added is generally in the range of from about 0.01 mole to about 0.15 mole of NaOH per mole of total hydrogen peroxide added in one embodiment; from about 0.02 mole to about 0.10 mole of NaOH per mole of total hydrogen peroxide added in another embodiment; and in the range of from about 0.04 mole to about 0.08 mole of NaOH per mole of total hydrogen peroxide added in yet another embodiment.

The reaction temperature of the reaction process of the present invention may vary depending on factors such as the particular nitrile and basic compounds being used. Generally, the temperature of the reaction may be maintained between about 20° C. and about 100° C. Temperatures in the range of from about 0° C. to about the boiling temperature of the mixture at the operating pressure can be employed, although temperatures of the order of from about 20° C. to about 100° C. may usually be used, preferably in a temperature range of from about 20° C. to about 60° C.; and more preferably in a temperature range of about 40° C. to about 50° C. In general, the higher the reaction temperature of the present invention process, the shorter will be the reaction time necessary to obtain high conversion of olefins. For example, reaction times as long as about 24 hours may be used at about 20° C., whereas when less than about 6 hours reaction time is desirable, the reaction temperature may be increased to about 50° C. In another embodiment, when operating above the boiling point of one or more reactants or solvents, it may be preferred to operate under sufficient pressure to maintain the reactants at least partially in the liquid phase.

In a different embodiment, the reaction temperature of the process of the present invention may be controlled by operating at the boiling point of a low boiling component of the reaction mixture, optionally at less than atmospheric pressure by applying vacuum, wherein at least a portion of vapors formed by boiling of the low boiling component(s) are condensed; and then optionally, the condensed vapors are recycled to the reaction mixture.

In the case of the epoxidation of divinylarenes which may be prone to free radical polymerization, temperatures of less than about 70° C. may be generally used to avoid undesired polymerization of the ethylenic double bonds, although temperatures of less than about 60° C. may be more preferred in another embodiment.

Numerous additives can optionally be employed as part of the present invention including for example, a free radical polymerization inhibitor. For example, one or more free radical polymerization inhibitors may be added to any of the steps of the process of the present invention including for instance the reaction step, the recovery step and/or the purification step. The inhibitor may comprise a phenol; a hydroquinone; a quinone; an aromatic nitro compound, a nitrophenol, an amine; a nitroso compound; a nitroxide; or mixtures thereof.

Free radical polymerization inhibitors which may be employed in the present invention, include for example phenols such as 4-methoxy phenol, 4-tert-butylcatechol, or 2,6-di-tert-butyl-4-methylphenol; hydroquinones such as 1,4-di-hyrdroxybenzene or 3,5-di-tert-butylbenzene-1,2-diol; quinones such as 1,4-benzoquinone or naphthalene-1,2-dione; aromatic nitro compounds such as 1,3-dinitrobenzene or 1,4-dinitrobenzene; nitrophenols such as 2-(sec-butyl)-4,6-dinitrophenol, 4-methyl-2-nitrophenol, or 4-methyl-2,6-dinitrophenol; amines such as phenothiazine, $N^1$-phenyl-$N^4$-propylbenzene-1,4-diamine, N-(1,4-dimethylpentyl)-N'phenyl-p-phenylenediamine, N,N-diethylhydroxylamine, or 2,2,6,6-tetramethylpiperidine; nitroso compounds such as N-nitrosophenylhydroxylamine ammonium salt; nitroxide compounds (described in detail herein below); or mixtures thereof.

Nitroxide compounds are a class of free radical polymerization inhibitors which are especially useful in the present invention. The term "nitroxides" as used here is synonymous with the terms "aminoxyl", "nitroxyl", or "hindered amine nitroxyl radicals" which are often used in the art. The nitroxides in general are compounds having at least one NO* group, where the * asterisk denotes an unpaired electron, and the nitrogen atom is bonded to two carbon atoms, to neither of which hydrogen atoms are attached. The nitroxide compounds useful in this invention have the generic structure:

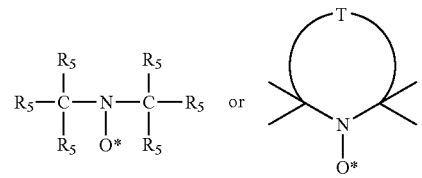

wherein each $R_5$ individually is an alkyl group of 1 to 18 carbon atoms and T is a group required to form a 5 or 6 member ring. Two or more nitroxyl groups may be present in the same molecule by linking two of the ring structures above through the T moiety by a linking group. Preferably, the nitroxides are selected from the group consisting of:
1-oxyl-2,2,6,6-tetramethylpiperidine (also referred to in the art as TEMPO),
1-oxyl-2,2,6,6-tetramethylpiperidin-4-ol (also referred to in the art as 4-hydroxy TEMPO),
1-oxyl-2,2,6,6-tetramethylpiperidin-4-one,
1-oxyl-2,2,6,6-tetramethyl-4-n-propoxypiperidine,
1-oxyl-2,2,6,6-tetramethyl-4-n-butoxypiperidine,
1-oxyl-2,2,6,6-tetramethyl-4-allyloxy-piperidine,
1-oxyl-2,2,6,6-tetramethyl-4-acetamidopiperidine,
1-oxyl-2,2,6,6-tetramethylpiperidin-4-(N-butylformamido) piperidine, 1-oxyl-2,2,6,6-tetramethyl-4-(2-methoxyethoxyacetoxy)piperidine,
1-oxyl-2,2,6,6-tetramethylpiperidin-4-yl stearate,
1-oxyl-2,2,6,6-tetramethylpiperidin-4-yl acetate,
1-oxyl-2,2,6,6-tetramethylpiperidin-4-yl butyrate,
1-oxyl-2,2,6,6-tetramethylpiperidin-4-yl 2-ethylhexanoate,
1-oxyl-2,2,6,6-tetramethylpiperidin-4-yl octanoate,
1-oxyl-2,2,6,6-tetramethylpiperidin-4-yl laurate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-(1-oxyl-2,2,6,6-tetramethylpiperidin-4-yl) adipamide,
N-(1-oxyl-2,2,6,6-tetramethylpiperidin-4-yl) caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl)]-s-triazine,
4,4'-ethylenebis(1-oxyl-2,2,6,6-tetramethylpiperazin-3-one),
1-oxyl-2,2,6,6-tetramethyl-4-(2,3-dihydroxypropoxy)piperidine,
1-oxyl-2,2,6,6-tetramethyl-4-(2-hydroxy-4-oxapentoxy)piperidine, and di-tert-butyl nitroxyl.

In one preferred embodiment, the nitroxide useful in the present invention may be selected from the group consisting of bis(1-oxyl-2,2,6,6-tetramethylpiperidin-4-yl) sebacate, 1-oxyl-2,2,6,6-tetramethylpiperidine, 1-oxyl-2,2,6,6-tetramethylpiperidin-4-ol, 1-oxyl-2,2,6,6-tetramethyl-4-n-butoxypiperidine and mixtures thereof.

A combination of inhibitors from within the same class (e.g. nitroxides), as described above, may be used; or a combination of inhibitors from above different classes may be used, for instance a phenolic inhibitor may be used in combination with a nitroxide.

In one embodiment, a combination of 4-tert-butylcatechol with either bis(1-oxyl-2,2,6,6-tetramethylpiperidin-4-yl) sebacate or 1-oxyl-2,2,6,6-tetramethylpiperidin-4-ol is used to inhibit free radical polymerization in the reaction to make a divinylarene dioxide such as DVBDO.

The free radical polymerization inhibitors introduced in the reaction step can be added in various forms (e.g., the inhibitor in its pure form or as a solution dissolved in a solvent) and with various methods of addition (such as for example: all at once, continuous, or intermittent). The concentration of the inhibitors useful in the present invention can be for example from about 0.01 wt % up to about 5 wt % based on total divinylarene added in the reaction. Preferably in another embodiment, the concentration of the inhibitors may be in the range of from about 0.1 wt % to about 2.0 wt % based on total divinylarene added in the reaction.

The inhibitors may be added all at the beginning of the reaction (prior to heating), intermittently (e.g. every 30 minutes), or continuously. A combination of addition methods can be used, for instance a portion of the total inhibitor may be added at the beginning of the reaction and the remaining portion of inhibitor can be added continuously during the reaction. When adding the inhibitor intermittently or continuously, the proportion of the total inhibitor added per time can be linear or non-linear. If using continuous inhibitor addition, the addition may be stopped for periods of time, especially toward the end of the reaction, which may give a higher efficiency of the inhibitor usage without sacrificing yield of the desired product.

The free radical polymerization inhibitor can be introduced either in its pure form or as a solution in a suitable solvent. The solvent used with the inhibitor can be for example any one or more of the same reaction solvents described above. For example, inhibitors can be introduced as solutions in any suitable solvent, including for instance water, methanol, acetonitrile, alkyl vinylarene monoxide (e.g. ethyl vinyl benzene monoxide), divinylarene (e.g. divinylbenzene), divinylarene monoxide (e.g. divinylbenzene monoxide), divinylarene dioxide (e.g. divinylbenzene dioxide), or mixtures thereof. In one embodiment, the inhibitor can be for example 1-oxyl-2,2,6,6-tetramethylpiperidin-4-ol, and can be introduced as a 20% solution in water during the reaction step.

In one preferred embodiment, the total amount of the free radical polymerization inhibitor added to the reaction mixture may comprise from about 0.01 wt % to about 5.0 wt % based on the total divinylarene added in the reaction. In another embodiment, the total amount of the free radical polymerization inhibitor added to the reaction mixture may be from about 0.1 wt % to about 2.0 wt % based on the total divinylarene added in the reaction. The free radical polymerization inhibitor may be added to the reaction mixture all at once, intermittently, continuously, or using a combination of addition methods, wherein the inhibitor may be added either in its pure form or in a suitable solvent.

In one preferred embodiment, the free radical polymerization inhibitor may comprise 1-oxyl-2,2,6,6-tetramethylpiperidine, or a substituted form of 1-oxyl-2,2,6,6-tetramethylpiperidine. In another embodiment, the free radical polymerization inhibitor may comprise 1-oxyl-2,2,6,6-tetramethylpiperidin-4-ol; 1-oxyl-2,2,6,6-tetramethyl-4-n-butoxypiperidine; bis(1-oxyl-2,2,6,6-tetramethylpiperidine-4yl) sebacate; 4-tert-butylcatechol; or mixtures thereof. In yet another embodiment, the free radical polymerization inhibitor may comprise bis(1-oxyl-2,2,6,6-tetramethylpiperidine-4yl) sebacate, which can be added intermittently or continuously over the course of the reaction at a total amount added to the reaction mixture of for example from about 0.1 wt % to about 2.0 wt % based on the total divinylarene added in the reaction. In still another embodiment, the free radical polymerization inhibitor may comprise 1-oxyl-2,2,6,6-tetramethylpiperidin-4-ol which can be added intermittently or continuously over the course of the reaction at a total amount added to the reaction mixture of for example from about 0.1 wt % to about 2.0 wt % based on the total divinylarene added in the reaction.

In another embodiment, the process of the present invention may optionally employ a free radical inhibitor alone, or in combination with an oxygen-containing gas; or the process can employ an oxygen-containing gas alone. In general, the oxygen-containing gas may be an oxygen-nitrogen gas mixture. In one embodiment, the oxygen-nitrogen gas mixture may comprise up to about 21% oxygen with the balance being nitrogen. In another embodiment, the oxygen-containing gas may be an oxygen-nitrogen gas mixture comprising up to about 10% oxygen with the balance being nitrogen. Generally, the flow rate of the gas mixture may comprise from about 0.01 to about 1.0 times the total reactor volume per minute.

In one embodiment, in conjunction with using free radical inhibitors that may require oxygen for activity, a vapor phase of the process can also include up to about 21% oxygen, with the balance comprising nitrogen. In other embodiments, the oxygen content of the gas may be generally up to about 21%, preferably up to about 10%, and more preferably up to about 5% with the balance being nitrogen or optionally another inert gas or mixtures of inert gases.

In another embodiment, the oxygen-containing gas may be introduced directly into a liquid phase of the process, optionally with stirring to help disperse the gas throughout the liquid phase in order to enhance the oxygen absorption into the liquid phase.

In one preferred embodiment, a gas composition with about 5% oxygen, with the balance nitrogen, is introduced continuously into the reaction directly into the liquid phase. The flow rate of the gas can be from about (0.01×the total reactor volume) per minute up to about (1.0×the total reactor volume) per minute. In another more preferred embodiment, the flow rate can be from about (0.05×the total reactor volume) per minute up to about (0.5×the total reactor volume) per minute.

Water may optionally be added to the initial reaction mixture (prior to addition of hydrogen peroxide or pre-formed peroxycarboximidic acid), generally, in an amount of from about 1 wt % to about 8 wt % with respect to the weight of initial reaction mixture.

Buffering agents such as alkali phosphates may also be optionally added to the reaction mixture in combination with the basic compounds Alkali phosphates which can be used in the present invention include for example sodium dihydrogen phosphate ($NaH_2PO_4$); potassium dihydrogen phosphate ($KH_2PO_4$); disodium hydrogen phosphate ($Na_2HPO_4$) either as its anhydrous or hydrated forms, for instance the dodecahydrate $Na_2HPO_4$ $12H_2O$; dipotassium hydrogen phosphate ($K_2HPO_4$); or mixtures thereof.

Chelating agents such as ethylenediaminetetraacetic acid or its dialkaline salt (e.g. disodium) may optionally be added to the initial reaction mixture in an amount from about 0.01 wt % to about 1 wt % with respect to the weight of hydrogen peroxide.

The reaction of the present invention may be carried in various ways including for example, as a batch process, as a semi-batch process, as a continuous process, or a combination thereof. Batch, intermittent, or continuous methods of reaction can be employed in the present invention; and the reactants can be introduced into the reaction mixture in any convenient order. In one preferred embodiment, the reaction may be carried out in (i) a batch fashion; or (ii) a continuous fashion. One advantageous method of batchwise reaction, when employing the procedure of in situ formation of the peroxycarboximidic acid epoxidizing agent, comprises adding hydrogen peroxide to the reaction mixture, for example, advantageously commercial aqueous hydrogen peroxide solution of about 30% to about 75% concentration, to a stirred mixture of the divinylarene compound being epoxidized, and an organic nitrile in a solvent containing sufficient base to bring the initial pH within the range in accordance with the present invention. Preferably the reaction mixture may be cooled while the hydrogen peroxide feed rate may be controlled so as to maintain the desired reaction temperature. Additional base can also be fed to the reaction mixture as needed to maintain the pH of the mixture within the range in accordance with the present invention. In an alternate embodiment, the total amount of the basic compound may be added to the reaction mixture at the start of the reaction in this method of operation. For example, basic acting salts, such as sodium bicarbonate, potassium phenoxide, sodium acetate, and the like; or mixtures thereof, may be used for maintaining the desired pH of the reaction in this way.

Alternatively, the reaction can be carried out by charging pre-formed peroxycarboximidic acid and a suitable solvent of the previously indicated type to a stirred reactor provided with temperature control means, suitably an autoclave, preferably with the desired base. Then, the divinylarene compound to be epoxidized may be fed into the reactor with or without additional basic compound as needed to maintain the pH of the reaction mixture within the preferred range until a reactor charge has been completed. For either order of addition above, it may be usually desirable to continue stirring the reaction mixture at the reaction temperature for a period of time after all of the reactants have been added in order to promote the desired degree of reaction, optionally with additional basic compound added to maintain the pH within the preferred range.

The process of the present invention can be carried out continuously in an apparatus of the forgoing type, for example, by partially reacting an initial charge as described above, then continuously adding divinylarene compound, hydrogen peroxide, and organic nitrile separately to the reactor with continuous or intermittent addition of base in the preferred amount while continuously or intermittently withdrawing divinylarene dioxide containing reacted mixture from the reactor. The same beneficial result can be obtained, by using a continuous stirred tank reactor (CSTR), a plug flow reactor (PFR), a loop reactor or a combination thereof, with or without external exchangers either in series or in parallel. A pump can be used to circulate the reaction mixture through the reactor as a continuous stream into which the divinylarene compound being epoxidized, hydrogen peroxide, nitrile and basic compound may be continuously fed at separate points sufficiently separated from the point of withdrawal of reaction mixture that substantial reaction may be achieved before removal of the product-containing mixture from the reactor.

Alternatively, the divinylarene compound can be fed at spaced points along the path of flow of the reaction mixture through a tubular or other suitable form of reactor in which the proper temperature may be maintained. Temperature control can be achieved by external cooling or evaporation of a volatile component of the mixture, for instance, a liquefied gaseous hydrocarbon such as butane or isopentane, which can also serve at least in part as the solvent and/or diluent for the reactants, the pressure of the system being regulated so that this volatile component will evaporate at the desired reaction temperature. As in the previously described modification of the process, hydrogen peroxide solution and/or a solution of the base being used can be fed, preferably separately, into the stream of reaction mixture at intermediate points between the points at which the divinylarene compound being epoxidized is fed. In any of these methods of operation a feed stream of pre-formed peroxycarboximidic acid can be substituted for the hydrogen peroxide and nitrile feeds. Advantageously, the peroxycarboximidic acid epoxidation agent may be fed as the crude reaction mixture in which it is produced, preferably at the alkaline pH at which the epoxidation is preferably conducted as previously described above.

The divinylarene dioxide produced by the process of the present invention can be recovered from the reaction mixture in any suitable manner, account being taken of the reactive nature of these compounds, especially the tendency of the epoxide ring to undergo hydration or alcoholysis in aqueous media, slowly under neutral conditions and more rapidly under acidic or basic conditions. One suitable method of recovering the divinylarene dioxide product may be by distillation. The distillation process may be used to obtain a divinylbenzene dioxide product with greater than about 80% purity in one embodiment; to obtain a divinylbenzene dioxide product with greater than about 90% purity in another embodiment; or to obtain a divinylbenzene dioxide product with greater than about 95% purity in yet another embodiment.

Depending on the relative boiling points of the divinylarene dioxide and the amide which may be obtained as the co-product therewith, the amide can be recovered before or after distilling off the divinylarene dioxide. For example, flash distillation under approximately neutral conditions, using reduced pressure, may be a preferred method for recovering the epoxide with or without the amide.

In another embodiment, extraction followed by distillation may be another method that can be used to recover the divinylarene dioxide. Extraction may be particularly effective to separate a water soluble amide co-product prior to distillation of the divinylarene dioxide product. For instance, when using acetonitrile to prepare the peroxyacetimidic acid epoxidizing agent, acetamide is formed as the co-product. Acetamide can be substantially separated from the divinylarene dioxide by extraction. The reaction mixture may be preferably diluted with additional water; and then extracted with a water insoluble organic extraction solvent to give (i) an aqueous layer containing most of the acetamide and methanol, or other water soluble reaction solvent; and (ii) an organic layer with most of the divinylarene dioxide product.

The organic extraction solvent useful in the present invention may comprise chlorinated organic solvents, ethers, aromatic hydrocarbons, ketones, esters, or mixtures thereof. Suitable organic extraction solvents include, for example, chlorinated organic solvents such as chloroform and methylene chloride; ethers such as diethyl ether; aromatic hydrocarbons such as benzene and toluene; ketones such as 4-methyl pentanone; esters such as ethyl acetate; or mixtures thereof. The divinylarene dioxide product in the organic solution may be optionally washed with water to remove any trace water soluble impurities, and then the extraction solvent may be removed by distillation, yielding a crude divinylarene dioxide product containing at least greater than about 50 wt % divinylarene dioxide present in the composition which can be used as is or further purified to increase the amount of divinylarene dioxide such as DVBDO in the product composition.

One embodiment of the above described method for purification of the divinylarene dioxide of the present invention, includes for example the following steps: (1) diluting the reaction mixture with water, (2) extracting the reaction mixture with a water insoluble extraction solvent such as chloroform, methylene chloride, diethyl ether, benzene, toluene or others, (3) water washing the resulting divinylarene dioxide-solvent layer, (4) removing the extraction solvent and residual water by distillation to yield a crude divinylarene dioxide product, and then, optionally, (5) distilling the crude divinylarene dioxide product to obtain a high purity divinylarene dioxide. Filtration may optionally be used in combination with this process or at any point in the reaction or purification steps to separate any solid impurities. For instance, in the case of benzamide as the co-product, the benzamide may precipitate during the extraction step; and filtration may be used to remove the benzamide from the divinylarene dioxide.

Any well known suitable means can be used to distill the crude divinylarene dioxide product including for example flash distillation. In one embodiment, the distillation may be carried out for example under the following conditions: Generally, the distillation may be carried out at a temperature of from about 60° C. to about 280° C. in one embodiment; from about 90° C. to about 200° C. in another embodiment; from about 100° C. to about 195° C. in yet another embodiment; and from about 130° C. to about 170° C. in still another embodiment. The pressure of the distillation may be generally from about 10 Pa to about 93000 Pa in one embodiment; from about 10 Pa to about 13000 Pa in another embodiment; from about 10 Pa to about 3300 Pa in yet another embodiment; and from about 10 Pa to about 2600 Pa in still another embodiment.

The purification distillation can be carried out in suitable equipment known to those skilled in the art including for example a wiped film evaporator, a falling film evaporator, a distillation column, a batch distill, and the like, or a combination thereof. The distillation/purification step of the present invention may comprise a batch process, semi-batch process, continuous process, or a combination thereof.

Thermal treatment of the divinylarene dioxide product of the present invention during the purification (e.g. distillation) step for an extended time can result in oligomer formation including for example oligomers such as dimers, trimers, and/or tetramers of the epoxide groups produced in the reaction step. To avoid oligomer formation, the purification may be done under vacuum conditions for longer periods of time at lower temperatures or under flash conditions for shorter periods of time at higher temperatures.

The oligomers formed from the divinylarene dioxide product with sustained heating during distillation, may create a situation where the oligomer containing divinylarene dioxide becomes too viscous to flow out of the processing apparatus, and may also result in loss of recovery of the divinylarene dioxide product. Accordingly, in one optional embodiment, a "high boiling point pot boiler" compound may be added to the feed stream passing to the purification process at a quantity sufficient to maintain a process stream's flowability in the equipment used in the present invention. For example, to maintain the flowability property of a process stream, a high boiling point pot boiler can be added generally at from about 5 wt % to about 50 wt %, preferably from about 5 wt % to about 40 wt %, more preferably from about 10 wt % to about 35 wt %, and even more preferably from about 20 wt % to about 30 wt %. The high boiling point pot boiler useful in the present invention generally has a boiling point higher than about 280° C. at 1 atm (101325 Pa) and a vapor pressure of about <20 Pa at 25° C.

Examples of the pot boiler suitable for use in the present invention include for example, mineral oils; liquid epoxy resins such as DER™ 383 and DER™ 331 (trademarks of The Dow Chemical Company); heat transfer fluids such as Thermia-C™ (trademark of Shell Company), Dowtherm MX™ (trademark of The Dow Chemical Company) and Dowtherm T™ (trademark of The Dow Chemical Company); or mixtures thereof. Optionally, the aforementioned embodiments of inhibitors and combinations thereof may be added to the purification steps or apparatuses to prevent the polymerization of residual ethylenic double bonds in the divinylarene dioxide product.

The reaction solvent, along with un-reacted nitrile present in the reaction effluent, and the optionally used extraction solvent can be recovered from any of the streams in the process of the present invention, including, for example: (1) recovery from the reaction mixture itself; (2) recovery from the water layer obtained from the extraction and water washes; (3) recovery from the organic layer from extraction or water washes; and (4) recovery from the crude divinylarene dioxide product prior to distillation. Recovery of reaction and/or extraction solvents and nitrile can be accomplished by any well-known means in the art, but may be preferably done by distillation.

The recovered amide co-product of the present reaction can be used in many known ways as a valuable compound. In one embodiment, it may be preferable to convert the amide co-product to a nitrile which can be recycled to the process to make more peroxycarboximidic acid epoxidizing agent for use in the process of the present invention. There are a number of methods available for converting the amide to a nitrile, for instance a method in which an amide may be reacted with phosphorous pentoxide or phosphorous pentachloride. Other methods which can be used to convert the amide to a nitrile are described in Beller et al., Chemical Communications, (2009), p 4883; and in Kologrivova et al., *Maslozhirovaya Promyshlennost*, (1978), vol. 11, pp 37-38, each herein incorporated by reference.

In one embodiment of the process of the present invention, the peroxycarboximidic acid may be generated in situ as described before. The process of the present invention may also include steps such as for example: (1) the recovery and recycle of all of the solvents used in the reaction or extraction step, (2) the recovery of the divinylarene monoxide, alkyl-vinyl-arene monoxide and/or divinylarene dioxide as separate streams; (3) the separation of the amide co-product of the reaction from the divinylarene dioxide product; (4) the conversion of the amide to a nitrile; and/or (5) the recycle of the converted nitrile in the epoxidation process. Any divinylarene monoxide formed in the process can be recycled to the reaction, to further convert the divinylarene monoxide to the divinylarene dioxide, or optionally, the divinylarene monoxide can be withdrawn from the process as a separate product stream. In addition, the use of any of the additives described herein can be used in combination with the process of the present invention.

With reference to FIG. 1, there is shown one embodiment of the process of the present invention, generally indicated by numeral 10 including a feed stream of divinylarene 31, a feed stream of an aqueous hydrogen peroxide 32, a feed stream of a basic compound 33, a feed stream of a nitrile compound 34, a feed stream of a free radical polymerization inhibitor 35, a feed stream of an oxygen-containing gas mixture 36, and a feed stream of a reaction solvent 37; all being fed to a reaction apparatus, herein reactor 30, for carrying out the reaction of the present invention. The product stream 38 from the reactor 30 may be introduced as a feed stream 38 to a separation/recovery apparatus, herein apparatus 40, wherein the divinylarene dioxide product stream 41 is separated from the other reaction components and recovered from the apparatus 40. For example, the reaction components can be separated from the divinylarene dioxide product in apparatus 40 and sent to a further processing unit, recovered, purged, and/or recycled such as an amide stream 42, a nitrile stream 43, a water stream 44 and a solvent stream 45. Any of the recycle streams may require a periodic or continuous purge to limit the buildup of impurities. An aqueous waste stream 46 may also be removed from apparatus 40 and sent to a waste recovery unit (not shown).

The product stream 41 from the apparatus 40 may then be introduced as a feed stream 41 to a purification process/apparatus, herein apparatus 50; wherein the product is further purified to form a purified product stream 51 leaving the apparatus 50. An organic waste stream 52 may also be removed from apparatus 50 and sent to an organic waste recovery unit (not shown). A stream 53 exiting from apparatus 50 may contain a divinylarene monoxide, an alkyl-vinyl-arene monoxide, or mixtures thereof; and said stream 53 may be purified to form a purified product stream (not shown) of a divinylarene monoxide, an alkyl-vinyl-arene monoxide, or mixtures thereof. In addition, the purified stream after being purified may be sent to a further processing unit, recovered, purged, and/or recycled.

With reference again to FIG. 1, in another optional embodiment, a portion or all of the amide stream 42 leaving the apparatus 40 may be sent to a conversion unit, herein apparatus 60, via stream 42a; wherein the amide stream may be converted to a nitrile by known means; and subsequently, the converted nitrile stream 61 from apparatus 60 may be recycled to the reactor 30 via feed stream 61. In an alternative embodiment, a waste stream 62 from apparatus 60 may exit apparatus 60 and optionally sent to further processing or a disposal unit.

Figure 2:
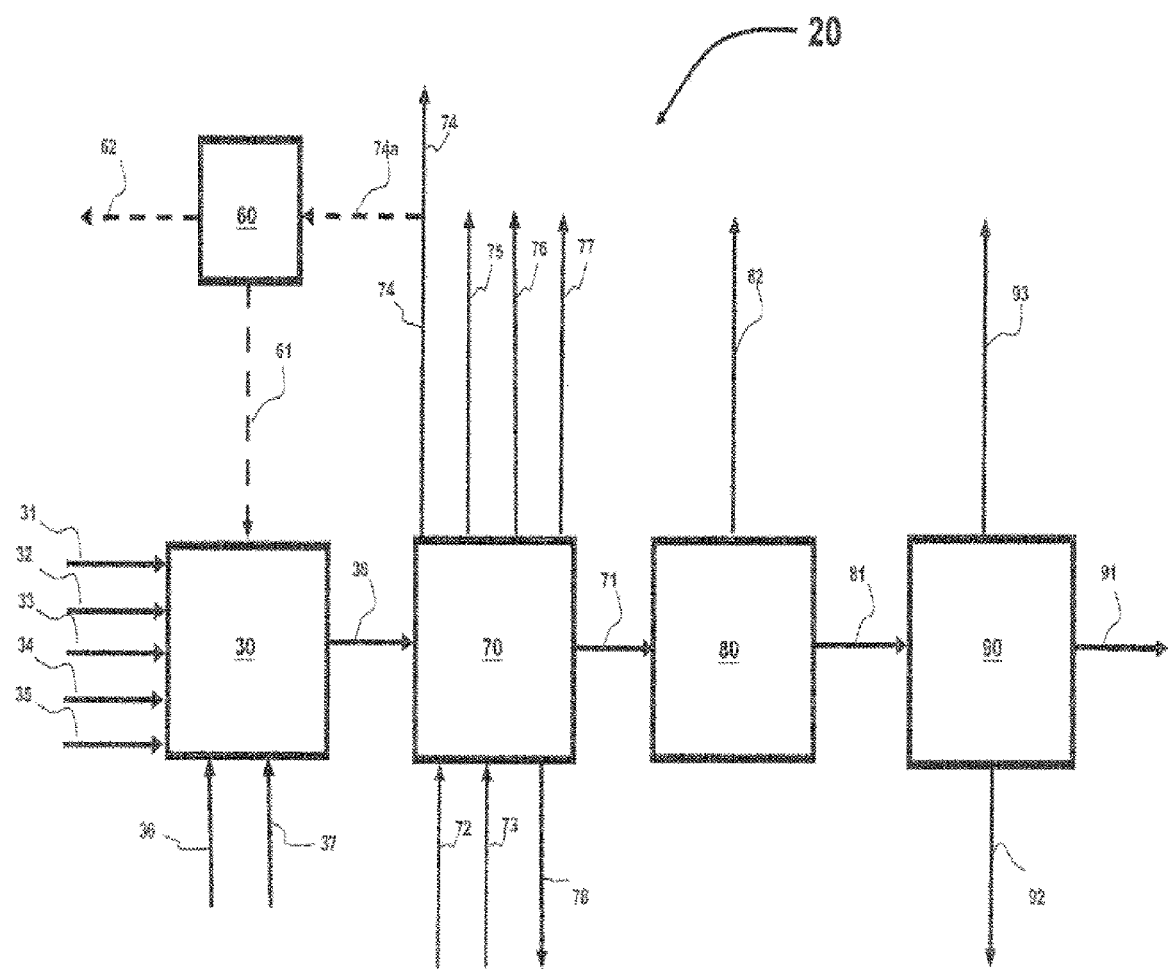
FIG. 2 is a block flow diagram showing another embodiment of the process of the present invention.

Now with reference to FIG. 2, there is shown another embodiment of the process of the present invention, generally indicated by numeral 20 including a feed stream of divinylarene 31, a feed stream of an aqueous hydrogen peroxide 32, a feed stream of a basic compound 33, a feed stream of a nitrile 34, a feed stream of a free radical polymerization inhibitor 35, a feed stream of an oxygen-containing gas mixture 36, and a feed stream of a reaction solvent 37; all being fed to a reaction apparatus, herein reactor 30, for carrying out the reaction of the present invention. In this embodiment, the product stream 38 from the reactor 30 may be introduced as a feed stream 38 to an extraction/water wash apparatus, herein apparatus 70; wherein the divinylarene dioxide product stream 71 is separated from the other reaction components and water washed in the apparatus 70. For example, an extraction solvent stream 72 and a water stream 73 are fed into the apparatus 70 to carry out the extraction/water wash. Then, for example, the reaction components can be separated from the divinylarene dioxide product in apparatus 70 by extraction and sent to a further processing unit, recovered, purged, and/or recycled such as an amide stream 74, a nitrile stream 75, a water stream 76 and an extraction solvent stream 77. Any of the recycle streams may require a periodic or continuous purge to limit the buildup of impurities. An aqueous waste stream 78 may also be removed from apparatus 70 and sent to a waste recovery unit (not shown).

The product stream 71 from the apparatus 70 may then be introduced to a extraction solvent recovery apparatus, herein apparatus 80, as a feed stream 71; wherein a product stream 81 exits the apparatus 80 and wherein the extraction solvent in the product may be separated and sent to further processing via extraction solvent stream 82.

The product stream 81 from the apparatus 80 may then be introduced to a purification process/apparatus, herein apparatus 90; wherein the product stream 81 is further purified to form a purified product stream 91 exiting the apparatus 90. An organic waste stream 92 may also be removed from apparatus 90 and sent to an organic waste recovery unit (not shown). A stream 93 exiting from apparatus 90 may contain a divinylarene monoxide, an alkyl-vinyl-arene monoxide, or mixtures thereof; and said stream 93 may be purified to form a purified product stream (not shown) of a divinylarene monoxide, an alkyl-vinyl-arene monoxide, or mixtures thereof. In addition, the purified stream after being purified may be sent to a further processing unit, recovered, purged, and/or recycled.

With reference again to FIG. 2, in another optional embodiment, a portion or all of the amide stream 74 leaving the apparatus 70 may be sent to a conversion unit, herein apparatus 60, via stream 74a, wherein the amide stream may be converted to a nitrile by known means, and subsequently, the converted nitrile stream 61 from apparatus 60 may be recycled to the reactor 30 via feed stream 61. In an alternative embodiment, a waste stream 62 from apparatus 60 may exit apparatus 60 and optionally sent to a further processing unit or a disposal unit.

The above process of the present invention may include one or more combinations of devices, instruments and equipment well known by one skilled in the art for processing the one or more effluents or streams of the process of the present invention, including for example vessels of any kind; such as reactors including batch reactors, semi-batch reactors, CSTRs, tubular reactors or combinations thereof; separators (batch, semi-batch or continuous), including for example stripping vessels, distillation columns, extraction units, filtration devices, flashes, evaporators, centrifuges, agitators; condensers; tubes; pipes; heat exchangers; storage tanks; pumps; compressors; valves; flanges; any internal element used within any of the above devices such as column packing; and any other equipment or connectors well known in the art for processing the products of the present invention and/or for the consumption of such products in another process.

The divinylarene dioxides prepared by the process of the present invention, particularly those derived from divinylbenzene such as for example divinylbenzene dioxide (DVBDO), are class of diepoxides which have a relatively low liquid viscosity but a higher rigidity than conventional epoxy resins.

The divinylarene dioxide prepared by the process of the present invention may comprise, for example, any substituted or unsubstituted arene nucleus bearing two vinyl groups in any ring position. The arene portion of the divinylarene dioxide may consist of benzene, substituted benzenes, or (substituted) ring-annulated benzenes or homologously bonded (substituted) benzenes, or mixtures thereof. The divinylarene portion of the divinylarene dioxide may be ortho, meta, or para isomers or any mixture thereof.

Additional substituents may consist of oxidant-resistant groups including saturated alkyl, aryl, halogen, nitro, isocyanate, or R'O—wherein R' may be the same as defined above. Ring-annulated benzenes may consist of naphthlalene, tetrahydronaphthalene, and the like. Homologously bonded (substituted) benzenes may consist of biphenyl, diphenylether, and the like.

The divinylarene dioxide product prepared by the process of the present invention may be illustrated generally by general chemical Structures V-VIII as follows:

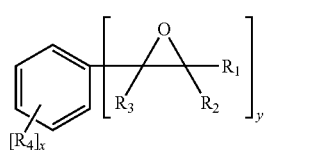

Structure V

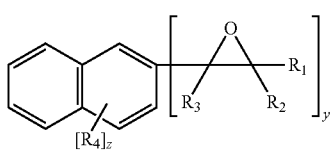

Structure VI

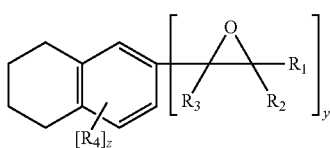

Structure VII

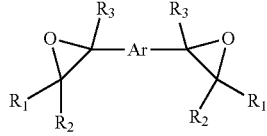

Structure VIII

In the above Structures V, VI, VII and VIII of the divinylarene dioxide product of the present invention, each $R_1$, $R_2$, $R_3$ and $R_4$ individually may be hydrogen, an alkyl, cycloalkyl, an aryl or an aralkyl group, where the alkyl, cycloalkyl, aryl, and aralkyl groups may have from 1 to about 18 carbon atoms, preferably from 1 to 4 carbon atoms; or a oxidant-resistant group including for example a halogen, a nitro, an isocyanate, or an R'O group, wherein R' may be an alkyl, aryl or aralkyl group having from 1 to about 18 carbon atoms, preferably from 1 to 4 carbon atoms; x may be an integer of 0 to 4; y may be an integer greater than or equal to 2; x+y may be an integer less than or equal to 6; z may be an integer of 0 to 6; z+y may be an integer less than or equal to 8; and Ar is an arene fragment including for example, 1,3-phenylene group.

The divinylarene dioxide product produced by the process of the present invention may include for example alkyl-vinylarene monoxides depending on the presence of alkyl-vinylarene in the starting material. The structure of the divinylarene dioxide, and composition of structural isomers, is determined by the divinylarene feedstock used. The reaction to epoxidize the ethylenic bonds do not generally impact the isomer distribution of the reactants as they are converted.

In one embodiment of the present invention, the divinylarene dioxide produced by the process of the present invention may include for example divinylbenzene dioxide, divinylnaphthalene dioxide, divinylbiphenyl dioxide, divinyldiphenylether dioxide, and mixtures thereof.

In a preferred embodiment of the present invention, the divinylarene dioxide used in the epoxy resin formulation may be for example DVBDO. Most preferably, the divinylarene dioxide component that is useful in the present invention includes, for example, a DVBDO as illustrated by the following chemical formula of Structure IX:

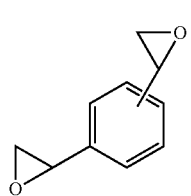

Structure IX

The chemical formula of the above DVBDO compound may be as follows: $C_{10}H_{10}O_2$; the molecular weight of the DVBDO is about 162.2; and the elemental analysis of the DVBDO is about: C, 74.06; H, 6.21; and O, 19.73 with an epoxide equivalent weight of about 81 g/mol.

Divinylarene dioxides, particularly those derived from divinylbenzene such as for example DVBDO, are class of diepoxides which have a relatively low liquid viscosity but a higher rigidity and crosslink density than conventional epoxy resins.

Structure X below illustrates an embodiment of a preferred chemical structure of the DVBDO useful in the present invention:

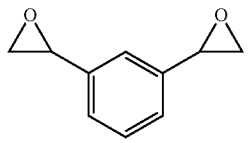

Structure X

Structure XI below illustrates another embodiment of a preferred chemical structure of the DVBDO useful in the present invention:

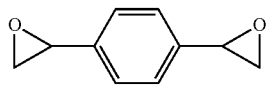

Structure XI

When DVBDO is prepared by the process of the present invention, it may be possible to obtain one of three possible isomers: ortho, meta, and para. Accordingly, the present invention includes a DVBDO illustrated by any one of the above structures individually or as a mixture thereof. Structures X and XI above show the meta (1,3-DVBDO) isomer of DVBDO and the para (1,4-DVBDO) isomer of DVBDO, respectively. The ortho isomer is rare; and usually DVBDO is mostly produced generally in a range of from about 9:1 to about 1:9 ratio of meta isomer (Structure X) to para isomer (Structure XI). The present invention preferably includes as one embodiment a range of from about 6:1 to about 1:6 ratio of Structure X to Structure XI, and in other embodiments the ratio of Structure X to Structure XI may be from about 4:1 to about 1:4 or from about 2:1 to about 1:2.

The structure of the divinylarene dioxide, and composition of structural isomers, is determined by the divinylarene feedstock used. In one embodiment, divinylbenzene feedstock with a meta:para ratio of generally in a range of from about 9:1 to about 1:9 is preferred. In another embodiment, the divinylbenzene feedstock may be from about 6:1 to about 1:6; from about 4:1 to about 1:4 in yet another embodiment; from about 2.5:1 to about 1:2.5 in still another embodiment; or from about 1.5:1 to about 1:1.5 another embodiment. In a preferred embodiment, the meta:para ratio of the divinylbenzene and the divinylbenzene dioxide both may range from about 9:1 to about 1:9 ratio; and in another embodiment, the meta:para ratio of the divinylbenzene and the divinylbenzene dioxide both may range from about 2.5:1 to abut 1:2.5 ratio.

The feedstock may also contain impurities including, but not limited to, ethylvinylbenzene (EVB), naphthalene, polyethylbenzenes (e.g. diethylbenzene, triethylbenzene, tetraethylbenzene, pentaethylbenzene, diphenylethane, other aklylated benzenes, and higher molecular weight oils), free radical inhibitors, or mixtures thereof. The divinylbenzene content of the feed may be greater than 55% in one embodiment; greater than 63% in another embodiment; greater than 80% in still another embodiment, greater than 90% in still another embodiment; or greater than 95% in yet another embodiment. The amount of co-product EVBO that is produced and that must be separated to obtain higher purity DVBDO is determined by DVB feed stock composition. In one preferred embodiment, the divinylarene feed stock purity may be greater than about 80 percent.

In one embodiment, the process of the present invention may be particularly suited for the preparation of divinylbenzene dioxide, a low viscosity liquid epoxy resin. The viscosity of the divinylarene dioxides produced by the process of the present invention ranges generally from about 10 mP-s to about 100 mP-s; preferably, from about 10 mP-s to about 50 mP-s; and more preferably, from about 10 mP-s to about 25 mP-s at 25° C.

The utility of the divinylarene dioxides of the present invention may be advantageously their thermal stability to allow their formulation or processing at moderate temperatures (for example, at from about 100° C. to about 200° C.) for up to several hours (for example, for at least 2 hours) without oligomerization or homopolymerization. Oligomerization or homopolymerization during formulation or processing may be evident by a substantial increase in viscosity or gelling (crosslinking) The divinylarene dioxides of the present invention have sufficient thermal stability such that they do not experience a substantial increase in viscosity or gelling during formulation or processing at moderate temperatures.

The divinylarene dioxide products of the present invention may be useful for the preparation of epoxy resin compositions or formulations which, in turn, may be useful for preparing thermosets or cured products in the form of coatings, films, adhesives, laminates, composites, electronics, and the like.

As an illustration of the present invention, in general, resin compositions based on the divinylarene dioxide products of the present invention may be useful for casting, potting, encapsulation, molding, and tooling. For example, the present invention may be used in electrical casting, applications; for plastic molding and tooling; and for the fabrication of composites parts.

An assortment of optional additives may be added to the resin composition of the present invention including for example, other resins, stabilizers, fillers, plasticizers, catalyst de-activators, and the like; and mixtures thereof.

The concentration of the optional additives used in the present invention may range generally from 0 wt % to about 99.9 wt %, preferably from about 0.1 wt % to about 99.9 wt %, more preferably from about 1 wt % to about 99 wt %, and most preferably from about 2 wt % to about 98 wt %.

EXAMPLES

The following examples and comparative examples further illustrate the present invention in detail but are not to be construed to limit the scope thereof.

The raw materials used in Examples 1-10 were as follows: divinylbenzene (DVB), 80% technical, obtained from Aldrich; acetonitrile (Optima® grade) obtained from Fisher Scientific; methanol (Optima® grade) obtained from Fisher Scientific; aqueous hydrogen peroxide, ~50% by weight, obtained from Aldrich (product #516183); sodium hydroxide (NaOH) solution, 1.0N concentration, obtained from Ricca Chemical Co. (product #7450-32); sodium bicarbonate obtained from Fisher Scientific; potassium bicarbonate obtained from Aldrich; and chloroform (Optima® grade) obtained from Fisher Scientific.

The yields in Examples 1-10 were calculated as follows:
Percent DVBDO Yield Based on Divinylbenzene Charged The yield of DVBDO in grams was calculated from the mass of crude reaction product obtained after extraction into chloroform and subsequent water washing and the weight ratio of DVBDO present in the crude product as measured by an internal standard gas chromatography (GC) method. The formulas used to calculate percent yield of DVBDO based on divinylbenzene charged may be written as follows:

DVBDO yield (gram)=(weight of crude product after water washing)×(weight ratio DVBDO in crude product).

Theoretical DVBDO yield based on DVB charged, gram=[(weight of DVB reagent charged)×(weight ratio of DVB in reagent)/(130.2 g DVB/mol)]×162.2 g DVBDO/mol.

DVBDO yield (%)=(DVBDO yield, gram/theoretical DVBDO yield, gram)×100%.

Percent Yield of Epoxide Based on Hydrogen Peroxide Charged

Total Epoxide produced, mole=[(DVBDO produced, gram)/(162.2 g/mol)]×2+(EVBO produced, gram)/(148 g/mol)+(DVBMO produced, gram)/(146 g/mol)] where the DVBDO, EVBO, and DVBMO mass produced was determined from the weight of crude product after water washing multiplied by the weight ratio of the component as determined by GC weight percent analysis.

Percent yield of epoxide based on hydrogen peroxide charged=[(total epoxide produced, mole)/hydrogen peroxide charged, mole]×100%.

Analytical Method for DVB, EVBO, DVBMO, and DVBDO Concentration by Gas Chromatography:

An Agilent HP-6890 Plus Series Gas Chromatograph (GC), equipped with a flame ionization detector, an auto injector, helium carrier gas and ChemStation software was used for GC analysis.

GC Operating Conditions Column: DB-1301 (30 m long by 0.250 mm I.D. by 1.00 μm film thickness).

Mode: Constant flow
Initial column flow: 1.1 mL/minute (mL/min)
Initial pressure: ~13.75 psi
Detector temperature: 300° C.
Injection Temperature: 280° C.
Injection volume: 1 microliter
Gas Flow rates.
Hydrogen flow: 40 mL/min
Air flow: 450 mL/min
Mode: Constant column+make-up flow
Combined flow: 45 mL/min
Helium flow:
  Total flow: ~58 mL/min
  Split flow: ~55 mL/min
  Split ratio: 50:1
GC Temperature Program:

Initial temperature 60° C., hold for 1 minute then ramp up at 10° C./minute to 150° C., at 2° C./minute to 180° C. hold for 5 minutes, then ramp at 10° C./minute to 250° C. and hold for 15 minutes.

GC Calibration:

A multilevel internal standard calibration was used to obtain the quantification of the components. Diglyme (bis-2-methoxyethyl ether) was the internal standard. Standards with the weight percent composition shown in the table below were prepared, and then 1.0 weight percent diglyme based on the total components weight was added. In the components listed below, m- and p-denote meta and para isomers, respectively.

| Components | Standard 1 Weight % | Standard 2 Weight % | Standard 3 Weight % |
|---|---|---|---|
| m-EVB | 0.0022 | 0.0107 | 0.1087 |
| p-EVB | 0.0017 | 0.0082 | 0.0831 |
| m-DVB | 0.0117 | 0.0563 | 0.5711 |
| p-DVB | 0.0050 | 0.0244 | 0.2470 |
| m-EVBO | 0.3373 | 3.2768 | 7.0273 |
| p-EVBO | 0.1923 | 1.8719 | 4.0117 |
| m-DVBDO | 0.2842 | 8.9720 | 14.6279 |
| p-DVBDO | 0.0957 | 3.0324 | 4.9416 |
| MeOH | 0.0213 | 1.0134 | 4.8282 |
| Acetonitrile | 0.0215 | 0.5714 | 4.8673 |
| Acetamide | 0.0500 | 0.1027 | 0.4963 |
| Chloroform | 98.9556 | 80.7568 | 57.6050 |

The standards were analyzed using the above GC method. A GC calibration table with amount/area ratios for each of the components and the internal standard was generated using the Agilent ChemStation software. An equation for the linear line through the calibration points was calculated by the software. The response factor for each component is obtained from the calibration equation for that component. For quantification of unknown samples, the actual amount of each component was calculated by the ChemStation software from the response of the component in the unknown, the response of the internal standard in the unknown, the actual weight of internal standard added to the unknown, and the response factor for the component which is calculated from the calibration equation. This calculation methodology can be found in product literature from Agilent (formerly Hewlitt Packard Company) ChemStation software.

GC Sample Preparation

The following two types of sample preparations were used:
(1) Standard GC Sample Preparation
(2) Chloroform Extraction GC Sample Preparation The procedures for each preparation above are described below.

Standard GC Sample Preparation:

| Step | Action |
|---|---|
| 1 | Weigh out 1-2 g of sample into a 1 or 2 dram vial using a 4 place balance. Record the weight. |
| 2 | Add 1% diglyme (e.g. 0.01-0.02 g) to the sample. Record the diglyme weight to the $4^{th}$ decimal place. |
| 3 | Mix the sample well then analyze the sample by GC. Enter the weights recorded above into ChemStation sequence. |

Chloroform Extraction GC Sample Preparation:

The extraction GC sample preparation is used for reaction samples because analysis of reaction samples by direct injection gives erroneous results due to the complex sample matrix. The procedure is as follows:

| Step | Action |
|---|---|
| 1 | Take ~1 g of a well-stirred reaction sample from the reactor and transfer the sample to a 3 or 4 dram vial. Record weight to 4 places. |
| 2 | Add an equal weight (~1 g) of water to the sample. |
| 3 | Add an equal weight (~1 g) of CHCl3 to the sample. |
| 4 | Mix the sample moderately for at least 1 minute, then centrifuge the sample to give rapid separation of the water and organic layers. |

-continued

| Step | Action |
|---|---|
| 5 | Pipette off the lower organic layer into a separate vial and record the weight to 4 places. |
| 6 | Add 1-2% diglyme (e.g. 0.02 × weight of organic layer from step 5) to the organic layer sample and record the weight of diglyme to 4 places. |
| 7 | Mix the sample well then analyze the sample by GC. |
| 8 | Sample Weights and Interpretation of Results: The weight of organic layer is entered as the sample weight and weight of diglyme is entered as ISTD weight in the ChemStation Sequence table. The multiplication factor is calculated by (wt of organic layer/wt of original reaction sample). The results for DVB, EVB, EVBO, DVBMO, and DVBDO are multiplied by the multiplication factor to give the concentration of these components in the reaction sample prior to extraction. |

The following table describes which GC sample preparation method was used for different types of samples.

| Sample Type | Sample Preparation and Results to Report |
|---|---|
| Reaction samples: | Chloroform Extraction GC Sample Prep. Report weight percent of DVB, EVB, EVBO, DVBMO, and DVBDO. |
| Organic and Aqueous Layers from Extraction and Water Wash: | Standard GC Sample Prep. Report weight percent of all calibrated components. |
| Organic layer after solvent strip: | Standard GC Sample Prep. Report weight percent of all calibrated components. |
| Distilled Product: | Standard GC Sample Prep. Report weight percent and area percent of all calibrated components. |

Analytical Method for Percent Heavies in Crude DVBDO

A gel permeation chromatography (GPC) method was used to measure the concentration (wt %) of heavies in the reaction product. The percent heavies is defined as the concentration in weight percent of molecules larger than the divinylbenzene dioxide. The method is summarized below.

GPC column: 50 Å with 5 μm particles, 300 mm long and 7.5 mm diameter; purchased from Polymer Labs
Injection size: 100 μL
Column and detector temp: 40° C.
Eluent: tetrahydrofuran (THF)
Detector: Refractive index (RI)
Reference Standard: 21000 g/mol polystyrene (PS)

The area of all peaks eluting before DVBDO in the GPC chromatogram are added together to give the total area count of heavies. The heavies are assumed to have the same refractive index as polystyrene. A series of standard solutions of different concentrations were prepared by serial dilution of a 5000 ppm PS standard. The RI area from injection of the standards was used to produce a linear calibration plot. The equation of the best fit line for RI area versus PS concentration was rearranged to solve for PS concentration.

Samples of the reaction mixture were extracted with chloroform prior to analysis, as described above in the GC analysis procedure, and the chloroform layer from the extraction was analyzed by GPC for percent heavies. Samples of the chloroform extract of the reaction mixture were prepared for analysis with about 1.0 g of the extract mixed well with about 2.0 g THF then filtered through a 0.2 micron filter prior to injection.

The GPC multiplication factor is calculated by the following equation:

(weight of extract+weight of THF)/weight of extract.

The heavies concentration in the sample injected is determined by substitution of the total area count of heavies into the calibration equation. The concentration (wt %) of heavies in the reaction mixture is obtained by multiplying the heavies concentration in the sample injected (wt %) by the GPC multiplication factor and by the chloroform extraction preparation multiplication factor.

Analytical Method for Hydrogen Peroxide Concentration

A 0.1-1 gram sample of the reaction mixture, weighed to the $4^{th}$ decimal place, was placed into a 250 mL flask. Glacial acetic acid (5 mL) was added then 40 mL of deionized water. Approximately 2 grams (g) of sodium iodide was next added to the flask. The mixture was stirred on a hot plate with medium heat. A small piece (4 g) of dry ice was added to the flask. Stirring was continued until the dry ice was consumed. An additional 120 mL of water was added to the flask, then the solution was titrated to an endpoint with 0.1N sodium thiosulfate solution using a Mettler Toledo DL55 automatic titrator equipped with DM140-SC electrode. The weight percent hydrogen peroxide in the sample is calculated as follows:

$$\text{wt \% H2O2} = \left(\frac{\text{Volume Na2S2O3, mL} * N_{Na2S2O3} * 34/2}{\text{sample wt, g} * 1000}\right) * 100$$

Example 1

Divinylbenzene (DVB) used in this Example 1 contained 80% DVB and 20% ethylvinylbenzene (EVB). Into a 1-L 5-neck round bottom flask was charged divinylbenzene (105 g, 0.645 mol DVB, 0.159 mol EVB), acetonitrile (88.1 g, 2.1453 mole), and methanol (210.1 g). The reaction flask was equipped with a Thermoscientific #8272BN pH probe connected to a Fisher Scientific accumet® AR15 pH meter. With vigorous stirring of the mixture, the resulting solution was warmed to 50° C., whereupon simultaneous addition of 51% $H_2O_2$ solution (72.1 g, 1.0807 mol) and 1N NaOH solution was begun. The $H_2O_2$ was added over a period of two hours while maintaining the reaction temperature at 50° C. and adding NaOH solution at a rate sufficient to maintain the pH at 11.0±0.2. After completion of the peroxide feed the mixture contained 0.72 wt % peroxide. The mixture was digested an additional 3 hours at 50° C. and pH 10.0-11.0 at which time the peroxide was 0.06 wt %. The mixture was diluted with 500 mL of water and extracted three times with 210 g of chloroform. The combined extracts were washed two times with water (240 g) yielding 657.7 g crude product which contained 9.1 g unreacted DVB, 5.39 g unreacted EVB, 14.0 g of ethylvinylbenzene oxide (EVBO), 40.28 g of divinylbenzene monoxide (DVBMO), and 34.4 g of DVBDO based on GC internal standard analysis. The unreacted DVB was 10.8% of the initial DVB charge. The DVBDO yield was 33% and the DVBMO yield was 43% based on DVB charged. The total yield of epoxide groups (summed for all three products EVBO, DVBMO, and DVBDO) was 74% based on $H_2O_2$ charged.

Example 2

Using the procedure described in Example 1, DVB (80.0 g, 0.4916 mole DVB, 0.1212 EVB), acetonitrile (95.85 g, 2.335 mole), and 51% $H_2O_2$ (77.86 g, 1.1675 mole) were reacted in methanol solvent (240 g) with pH controlled at 11.0±0.2 by addition of 1N NaOH. The unreacted DVB was 1.0% of the initial DVB charged. The DVBDO yield was 65% and the DVBMO yield was 19% based on DVB charged. The total yield of epoxide groups (summed for all three products EVBO, DVBMO, and DVBDO) was 71% based on $H_2O_2$ charged.

Example 3

Using the procedure described in Example 1, DVB (67.0 g, 0.4117 mole DVB, 0.1015 mole EVB), acetonitrile (98.72 g, 2.4044 mole), and 51% $H_2O_2$ (80.19 g, 1.2022 mole) were reacted in methanol solvent (234.5 g) with pH controlled at 11.0±0.2 by addition of 1N NaOH. The unreacted DVB was 0.1% of the initial DVB charge. The DVBDO yield was 78% and the DVBMO yield was 7% based on DVB charged. The total yield of epoxide groups (summed for all three products EVBO, DVBMO, and DVBDO) was 63% based on $H_2O_2$ charged.

Example 4

Using the procedure described in Example 1, DVB (67.0 g, 0.4117 mole DVB, 0.1015 mole EVB), acetonitrile (98.7 g, 2.4044 mole), and 51% $H_2O_2$ (80.17 g, 1.2022 mole) were reacted in methanol solvent (234.5 g) with pH controlled at 10.4±0.2 by addition of 1N NaOH. The DVB conversion was 100%. The DVBDO yield was 81% and the DVBMO yield was 4% based on DVB charged. The total yield of epoxide groups (summed for all three products EVBO, DVBMO, and DVBDO) was 65% based on $H_2O_2$ charged.

Example 5

This Example 5 shows the use of benzonitrile and sodium bicarbonate in place of acetonitrile and alkali. The reactor setup was the same as in Example 1 except no pH meter or caustic addition funnel was used. Into a 1-L 5-neck round bottom flask was charged DVB (65 g, 0.399 mol DVB, 0.098 mol EVB), benzonitrile (97.2 g, .942 mole), methanol (292.6 g), and sodium bicarbonate (12.66 g, 0.151 mole). With vigorous stirring of the mixture at 25° C., addition of 51% $H_2O_2$ solution (62.9 g, 0.942 mol) was begun.

The $H_2O_2$ was added over a period of 30 minutes while maintaining the reaction temperature at 25° C. After completion of the $H_2O_2$ feed the mixture was stirred an additional 18 hours at 25° C. after which the $H_2O_2$ was 0.58 wt %. The temperature was gradually increased to 45° C. over 1 hour; then maintained at 45° C. for an additional 1.5 hour at which time the $H_2O_2$ remaining was 0.45%. The mixture was diluted with 600 mL of water and extracted three times with 200 g of chloroform. The combined extracts were washed three times with water (300 g) yielding 493 g crude product which contained 0.15 g unreacted DVB, 0.44 g unreacted EVB, 12.87 g of EVBO, 7.69 g of DVBMO, and 52.5 g of DVBDO based on GC internal standard analysis. The unreacted DVB was 0.3% of the initial DVB charge. The DVBDO yield was 81% and the DVBMO yield was 13% based on DVB charged. The total yield of epoxide groups (summed for all three products EVBO, DVBMO, and DVBDO) was 97% based on $H_2O_2$ charged.

Example 6

DVB (67.0 g, 0.4117 mole DVB, 0.1015 mole EVB), acetonitrile (98.7 g, 2.4044 mole), and 51% $H_2O_2$ (80.17 g, 1.2022 mole) were reacted in methanol solvent (234.5 g) according to the procedure in Example 1 except that the pH was controlled at 10.0 - 10.1 by addition of 1N NaOH and the digest time after $H_2O_2$ addition was four hours. A total of 94.2 g of 1N NaOH (0.090 mol) was added in a total reaction time of six hours. The reaction product was extracted into chloroform and washed with water as in Example 1.1 Solvent was removed by distillation giving 76.8 g of crude product. DVB conversion was 100%, DVBDO yield was 88%, and DVBMO yield was 2% based on DVB charged. The total yield of epoxide groups (summed for all three products EVBO, DVBMO, and DVBDO) was 69% based on $H_2O_2$ charged. Distillation of the crude at 128° C. overhead temperature and 3 mmHg (400 Pa) pressure gave 17.8 g of a first distillate with 67.7% EVBO, 3.71% DVBMO, and 25.5% DVBDO, based on GC area percent analysis. Further distillation at 133° C. overheads and 3 mmHg (400 Pa) pressure gave 44.5 g of DVBDO with 97.7% purity by GC area percent, with only 0.1% of residual DVBMO.

Example 7

The procedure of Example 6 was repeated except that water (20.0 g, 5 wt % based on initial reaction mixture) was added to the initial reaction mixture prior to adding any $H_2O_2$ or NaOH solution. A total of 96.4 g of 1N NaOH (0.093 mole) was added in a total reaction time of five hours. After workup and distillation to remove solvent, the yield of crude product was 75.2 g. DVB conversion was 100%, DVBDO yield was 86%, and DVBMO yield was 2%. The total yield of epoxide groups (summed for all three products EVBO, DVBMO, and DVBDO) was 67% based on $H_2O_2$ charged.

Example 8

This Example 8 illustrates the use of a NaOH addition profile instead of adding NaOH to control pH. The procedure of Example 7 was repeated except 96.4 g of 1N NaOH was added at 0.11 mL/minute for the first 100 minutes then at 0.40 mL/minute for the remaining 200 minutes. After workup and distillation to remove solvent, the yield of crude product was 73.9 g. DVB conversion was 100%, DVBDO yield was 85%, and DVBMO yield was 2%. The total yield of epoxide groups was 67% based on $H_2O_2$ charged.

Example 9

This Example 9 shows the use of acetonitrile with sodium bicarbonate as the basic compound. The reactor setup was the same as in Example 1 except no caustic addition funnel was used. Into a 1-L 5-neck round bottom flask was charged divinylbenzene (75.17 g, 0.4609 mol DVB, 0.1135 mol EVB), acetonitrile (110.5 g, 2.6915 mole), methanol (262.5 g), and potassium bicarbonate (21.63 g, 0.2160 mole). With vigorous stirring of the mixture at 25° C., addition of 51% $H_2O_2$ solution (89.8 g, 1.3458 mole) was begun. The $H_2O_2$ was added over a period of 120 minutes while maintaining the reaction temperature at 25° C. After completion of the peroxide feed the mixture was stirred an additional 20 hours at 25° C. after which the peroxide was 1.50 wt %. The temperature was gradually increased to 45° C. over 1 hour then maintained at 45° C. for an additional 2 hours at which time the peroxide remaining was 0.45%. The mixture was diluted with 500 mL of water and extracted three times with 200 g of chloroform. The combined extracts were washed three times with 150 g of water yielding 637 g crude product which contained 0.06 g unreacted DVB, 0.19 g unreacted EVB, 15.41 g of EVBO, 5.86 g of DVBMO, and 61.79 g of DVBDO based on GC internal standard analysis. The unreacted DVB was 0.1% of the initial DVB charge. The DVBDO yield was 83% and the DVBMO yield was 9% based on DVB charged. The total yield of epoxide groups (summed for all three products EVBO, DVBMO, and DVBDO) was 69% based on $H_2O_2$ charged.

Example 10

Using the procedure described in Example 1, DVB (58.0 g, 0.3564 mole DVB, 0.0877 mole EVB), acetonitrile (105.37 g, 2.5618 mole), and 51% $H_2O_2$ (85.42 g, 1.2809 mole) were reacted in methanol solvent (232 g) with pH controlled at 11.0±0.2 by addition of 1N NaOH. The unreacted DVB was 0.1% of the initial DVB charge. The DVBDO yield was 77% and the DVBMO yield was 6% based on DVB charged. The total yield of epoxide groups (summed for all three products EVBO, DVBMO, and DVBDO) was 51% based on $H_2O_2$ charged.

The conditions and results of Examples 1-10 are summarized in Table I as follows:

used to calculate percent yield of DVBDO based on divinylbenzene charged may be written as follows:

DVBDO yield (gram)=(weight of reaction product)× (weight ratio DVBDO in reaction product).

Theoretical DVBDO yield based on DVB charged, gram=[(weight of DVB reagent charged)× (weight ratio of DVB in reagent)/(130.2 g DVB/mol)]×162.2 g DVBDO/mol.

DVBDO yield (%)=(DVBDO yield, gram/theoretical DVBDO yield, gram)×100%.

Percent Yield of Epoxide Based on Hydrogen Peroxide Charged

Total Epoxide produced, mole=[(DVBDO produced, gram)/(162.2 g/mol)]×2+(EVBO produced, gram)/(148 g/mol)+(DVBMO produced, gram)/(146 g/mol)] where the DVBDO, EVBO, and DVBMO mass produced was determined from the weight of final reaction product multiplied by the weight ratio of the component as determined by GC weight percent analysis.

TABLE I

| Example # | Basic Comp. | Nitrile[a] | $H_2O_2$/ C=C equiv. | pH[b] | Temp. (°C.) | Reaction time (hr) | $H_2O_2$ conv. (%) | DVB conv. (%) | DVBMO yield (%)[i] | DVBDO yield (%)[i] | Epoxide yield (%)[g] |
|---|---|---|---|---|---|---|---|---|---|---|---|
| 1 | NaOH | ACN | 0.75 | 11.0-11.2 | 50 | 5 | 99.2 | 89.2 | 43 | 33 | 74 |
| 2 | NaOH | ACN | 1.06 | 11.0-11.2 | 50 | 4 | 96.0 | 99.0 | 19 | 65 | 71 |
| 3 | NaOH | ACN | 1.30 | 11.0-11.2 | 50 | 5 | 98.3 | 99.9 | 7 | 78 | 63 |
| 4 | NaOH | ACN | 1.30 | 10.3-10.4 | 50 | 5 | 95.3 | 100 | 4 | 81 | 65 |
| 5[e] | NaHCO₃ | BN | 1.05 | nd[h] | 25-45[e] | 22 | 93.3 | 99.7 | 13 | 81 | 97 |
| 6 | NaOH | ACN | 1.30 | 10.0-10.1 | 50 | 6 | 91.9 | 100 | 2 | 88 | 69 |
| 7[c] | NaOH | ACN | 1.30 | 10.0-10.1 | 50 | 5 | 97.0 | 100 | 2 | 86 | 67 |
| 8[d] | NaOH | ACN | 1.30 | 9.5-0.8 | 50 | 5 | 96.2 | 100 | 2 | 85 | 67 |
| 9[f] | KHCO₃ | ACN | 1.30 | 9.5-1.3 | 25-45[f] | 25 | 95.2 | 99.9 | 9 | 83 | 69 |
| 10 | NaOH | ACN | 1.60 | 11.0-11.2 | 50 | 4.5 | 98.7 | 99.9 | 6 | 77 | 51 |

[a]ACN = acetonitrile, BN = benzonitrile.
[b]This is the indicated pH from the pH meter.
[c]Example 7 had 5% water added to the initial reaction mixture.
[d]Example 8 had 5% water added to the initial reaction mixture and did not use pH control. Instead, 1N NaOH was added at 0.11 mL/minute from 0-100 minutes and at 0.40 mL/minute from 200-300 minutes.
[e]Example 5 - reacted at 25° C. for 19 hours, then 45° C. for 1.5 hours.
[f]Example 9 - reacted at 25° C. for 22 hours, then 45° C. for 2.5 hours.
[g]Percent yield of epoxide groups (summed for ethylvinylbenzene oxide, divinylbenzene monoxide, and divinylbenzene dioxide) based on the total hydrogen peroxide added.
[h]"nd" = "not determined."
[i]DVBMO and DVBDO percent yields based on charged DVB.

Examples 11 through 15 and Comparative Examples A and B which follow further illustrate the present invention in detail but are not to be construed to limit the scope thereof. The raw materials used in Examples 11-15 and Comparative Examples A and B were as follows: divinylbenzene (DVB), 80% or 95% purity, (obtained from The Dow Chemical Company), acetonitrile (high purity) obtained from INEOS chemical company, methanol (technical grade) obtained from Fisher Scientific; aqueous hydrogen peroxide, ~35% by weight, obtained from Univar; and sodium hydroxide (NaOH) solution, 4 wt % was prepared by dilution of 50% caustic obtained from Fisher Scientific.

The yields in Examples 11-15 and Comparative Examples A and B were calculated as follows:

Percent DVBDO Yield Based on Divinylbenzene Charged

The yield of DVBDO in grams was calculated from the weight of final reaction product obtained (without chloroform extraction or water washing) and the weight ratio of DVBDO present in the reaction product as measured by an internal standard gas chromatography (GC) method. The formulas Percent yield of epoxide based on hydrogen peroxide charged=[(total epoxide produced, mole)/hydrogen peroxide charged, mole]×100%.

Example 11

Divinylbenzene raw material used in this Example 11 contained 80% DVB and 20% EVB. Into a 1-L 5-neck round bottom flask was charged the divinylbenzene (80 g, 0.4916 mol DVB, 0.1210 mol EVB), acetonitrile (117.85 g, 2.8709 mol), methanol (160.0 g) and water (17.9 g). The reaction flask was equipped with a pH meter as described in Example 1.1 With vigorous stirring of the mixture, the resulting solution was warmed to 45° C., whereupon addition of 35% $H_2O_2$ was begun at 0.58 grams/minute (g/min) flow rate, with the addition continued for a period of 4 hours for a total of 139.0 g (1.4355 mol) of $H_2O_2$ solution added. Simultaneous dropwise addition of 4.0 wt % NaOH solution was begun 14 minutes after beginning the $H_2O_2$ addition, with the NaOH addition rate controlled to maintain the pH at 10.0±0.1 for the total reaction period of five hours. The total weight of NaOH solution required was 113.1 g (0.1131 mol). The reaction temperature was allowed to gradually rise from the heat of the reaction up to 50° C. at 105 minutes, then the temperature was maintained at 50° C. for the remainder of the reaction. The reaction was sampled for GC analysis at five hours, then cooled to ambient temperature (about 22° C.).

The mixture was discharged from the reactor yielding 592 g of reaction product. The DVB conversion was 100% and the $H_2O_2$ conversion was 92.8%. The DVBDO yield was 80% and the DVBMO yield was 1%. The total yield of epoxide groups (summed for all three products EVBO, DVBMO, and DVBDO) was 61% based on $H_2O_2$ charged.

Example 12

The procedure of Example 11 was repeated except the pH of the mixture was controlled at 10.5.1 Divinylbenzene (75.0 g, 0.4609 mol of DVB, 0.1135 mol of EVB), acetonitrile (110.5 g), methanol (150 g), water (16.7 g) were charged initially followed by addition of 35% $H_2O_2$ (130.3 g, 1.3458 mol) over four hours. The pH was controlled at 10.5±0.1 for the total reaction time of 4.7 hours by dropwise addition of 4 wt % NaOH (168.2 g, 0.202 mol). At the end of the reaction, the DVB conversion was 99.9% and the $H_2O_2$ conversion was 96.2%. The DVBDO yield was 66% and the DVBMO yield was 2%. The total yield of epoxide groups (summed for all three products EVBO, DVBMO, and DVBDO) was 51% based on $H_2O_2$ charged.

Comparative Example A

The procedure of Example 11 was repeated except the pH of the mixture was controlled at 11.0.1 This Comparative Example A illustrates the disadvantage of operating at too high a pH during the reaction. Divinylbenzene (80 g, 0.4916 mol DVB, 0.1210 mol EVB), acetonitrile (117.85 g, 2.8709 mol), methanol (160.0 g) and water (17.9 g) were added to the reactor followed by addition of 35% $H_2O_2$ (139.0 g, 1.4355 mol) over four hours. The pH was controlled at 11.0 by dropwise addition of 4 wt % NaOH (246.5 g, 0.2465 mol) from 14 to 220 minutes, then by dropwise addition of 25 wt % NaOH (18.0 g, 0.1125 mol) from 220 to 270 minutes, at which point the reaction was halted. Visible solids (identified as poly-DVB type polymer) were present in the reaction mixture. The DVB conversion was 98.0% and the $H_2O_2$ conversion was 98.7%. The DVBDO yield was 32% and the DVBMO yield was 11%. The total yield of epoxide groups (summed for all three products EVBO, DVBMO, and DVBDO) was 30% based on $H_2O_2$ charged.

Example 13

In this Example 13, the procedure of Example 11 was repeated except the pH of the mixture was controlled at 9.5.1 Divinylbenzene (80.0 g, 0.4916 mol of DVB, 0.1210 mol of EVB), acetonitrile (117.9 g), methanol (160 g), and water (17.9 g) were charged followed by addition of 35% $H_2O_2$ (139.0 g, 1.4355 mol) over four hours. The pH was controlled at 9.5±0.1 for the total reaction time of five hours by dropwise addition of 4 wt % NaOH (86.0 g, 0.086 mol). At the end of the reaction, the DVB conversion was 99.9% and the $H_2O_2$ conversion was 89.0%. The DVBDO yield was 83% and the DVBMO yield was 1.6%. The total yield of epoxide groups (summed for all three products EVBO, DVBMO, and DVBDO) was 62% based on $H_2O_2$ charged.

The conditions and results of Examples 11-13 and Comparative Example A are summarized in Table II as follows.

TABLE II

| Example # | pH[a] | NaOH/ $H_2O_2$ mole[b] | Temp. (° C.) | Reaction time (hr) | $H_2O_2$ conv. (%) | DVB conv. (%) | DVBMO yield based on DVB (%) | DVBDO yield based on DVB (%) | Epoxide yield based on $H_2O_2$ (%) |
|---|---|---|---|---|---|---|---|---|---|
| 13 | 9.5 ± 0.1 | 0.060 | 45-50 | 5.0 | 89.0 | 99.9 | 2 | 83 | 62 |
| 11 | 10.0 ± 0.1 | 0.079 | 45-50 | 5.0 | 92.8 | 100 | 1 | 80 | 61 |
| 12 | 10.5 ± 0.1 | 0.125 | 45-50 | 4.7 | 96.2 | 99.9 | 2 | 66 | 51 |
| Comp. Ex. A | 11.0 ± 0.1 | 0.250 | 45-50 | 4.5 | 98.7 | 98.0 | 11 | 32 | 30 |

[a]This is the indicated pH from the pH meter. The pH was maintained in this range for the entire reaction.
[b]Total mole NaOH added per total mole of $H_2O_2$ added over the entire reaction period.

Examples 14 and Comparative Example B were made in a 30 gallons (114 L) stainless steel reactor [20-inch (51 cm) I.D., 20-inch (51 cm) straight wall, 24.75-inch (63 cm) height] equipped with four 1-inch (2.5 cm) baffles at 90 degree intervals. The reactor was jacketed with temperature control achieved by control of the temperature of the heat transfer fluid circulated through the jacket. The reactor was equipped with a condenser, 4 inch (10 cm) by 48 inch (122 cm), straight tube. The condenser was set at 0° C. during the reaction. Hydrogen peroxide solution and NaOH solution were metered in from separate feed vessels each placed on a scale to measure the weight change with time. Agitation was provided with a 12 inch (30.5 cm) A-310 impeller operating at 200 rpm. A gas mixture with 5% oxygen, balance nitrogen, was introduced continuously into the liquid phase of the reaction mixture. The gas mixture was introduced into the liquid through a dip tube at a flow rate of 0.9 scfm (25.5 liters per minute), which provides about 0.25 turnovers per minute.

Example 14

This Example 14 illustrates a scale-up of the reaction in the 114-L reactor described above with multiple additions of an inhibitor, PROSTAB™5415 used for minimizing free radical polymerization of DVB. PROSTAB 5415 is an inhibitor commercially available from BASF Corporation. PROSTAB 5415 is bis(1-oxyl-2,2,6,6-tetramethylpiperidine-4yl) sebacate.

Free radical polymerization was not observed in small scale lab runs at a pH of 9.5-10.1 However, upon scaling up these conditions to a 30 gallon (114 L) stainless steel reactor, free radical polymerization was observed. In addition to the inhibitors present in the DVB raw material, additional PROSTAB 5415 was added to the initial reaction mixture prior to heating and subsequent additions of PROSTAB 5415 were made at 30 minute intervals to make up for PROSTAB 5415 consumed in the process.

Divinylbenzene raw material contained 94% DVB and 4% EVB, with 1500 ppm PROSTAB 5415 and 1000 ppm 4-tert-butyl catechol (TBC) present as polymerization inhibitors. Into the 30-gallon (114 L) stainless steel reactor described above was charged divinylbenzene (10750 g, 77.34 mol DVB, 2.976 mol EVB), acetonitrile (17178 g, 418.48 mol), methanol (21500 g), PROSTAB 5415 solid (26.9 g, 0.0527 mol), and water (2472 g). Introduction of 5% oxygen, balance nitrogen gas was begun into the liquid at 0.9 scfm (25.5 liters per minute). With stirring of the mixture at 200 rpm, the resulting solution was warmed to 45° C. whereupon addition of 35% $H_2O_2$ was begun at ~87 g/min flow rate, with the addition continued for a period of 4 hours for a total of 20997 g (216.1 mol) of $H_2O_2$ added. Simultaneous addition of 4.0 wt % NaOH solution was begun 10 minutes after beginning the $H_2O_2$ addition. The NaOH solution was added throughout the reaction using the following flow rate profile:

| Reaction Time Period | Flow rate (g/min) | Total NaOH solution added for period (g) | % of total NaOH |
|---|---|---|---|
| 10-200 min: | 24.1 | 4286.5 | 33.2 |
| 200-300 min: | 86.3 | 8627.5 | 66.8 |

The total amount of 4 wt % NaOH solution added was 12914 g (12.91 mol). In addition to the initial amount of PROSTAB 5415 added prior to heating, a solution of 5 wt % PROSTAB 5415 in methanol was added every 30 minutes during the reaction as shown in the table below.

| Reaction Time | 5 wt % PROSTAB 5415 added (g) |
|---|---|
| 30 | 484 |
| 60 | 484 |
| 90 | 484 |
| 120 | 322 |
| 150 | 322 |
| 180 | 355 |
| 210 | 161 |
| 240 | 140 |
| 270 | 137 |

The reaction temperature was allowed to gradually rise from 45° C. to 50° C., and then the temperature was maintained at 50° C. for the remainder of the reaction. The NaOH feed was stopped at five hours, which was the end of the reaction, and the reaction was sampled for GC analysis while still stirring vigorously. The total weight of the final reaction mixture was 83751 g which contained 12.93 wt % DVBDO based on GC analysis, 0.69 wt % $H_2O_2$ based on titration, and 0.48 wt % heavy species by GPC. The DVB conversion was 99.9% and the $H_2O_2$ conversion was 92.1%. The DVBDO yield was 85% and the DVBMO yield was 1.6%. The total yield of epoxide groups (summed for all three products EVBO, DVBMO, and DVBDO) was 64% based on $H_2O_2$ charged.

Comparative Example B

The same procedure and raw materials used in Example 14 were used in this Comparative Example B except without any additional PROSTAB 5415 added to the reaction mixture. Divinylbenzene raw material contained 94% DVB and 4% EVB, with 1500 ppm PROSTAB 5415 and 1000 ppm 4-tert-butyl catechol (TBC) present as polymerization inhibitors. Into the 30 gallon (114 L) stainless steel reactor described above was charged divinylbenzene (10752 g, 77.318 mol DVB, 2.977 mol EVB), acetonitrile (17178 g, 418.48 mol), methanol (21521 g), and water (2472 g). Introduction of 5% oxygen, balance nitrogen gas was begun into the liquid at 0.9 scfm (25.5 liters per minute). With stirring of the mixture at 200 rpm, the resulting solution was warmed to 45° C. whereupon addition of 35% $H_2O_2$ was begun at ~82 g/min flow rate, with the addition continued for a period of 4.2 hours for a total of 20508 g (211.0 mol $H_2O_2$) added. Simultaneous addition of 4.0 wt % NaOH solution was begun 10 minutes after beginning the $H_2O_2$ addition. The NaOH solution was added throughout the reaction using the following flow rate profile:

| Reaction Time Period | Flow rate (g/min) | Total NaOH solution added for period (g) | % of Total NaOH |
|---|---|---|---|
| 10-200 minutes | 24.2 | 4608.5 | 34.8 |
| 200-300 minutes | 86.3 | 8627.5 | 65.2 |

The total amount of 4 wt % NaOH solution added was 13236 g (13.2 mol). The reaction temperature was allowed to gradually rise from 45° C. to a 50° C., and then the temperature was maintained at 50° C. for the remainder of the reaction. Solids (polymer) were observed in reaction samples starting at 30 minutes. The NaOH feed was stopped at five hours, which was the end of the reaction, and the reaction was sampled for GC analysis while still stirring vigorously. The total weight of the final reaction mixture was 83237 g which contained 9.3 wt % DVBDO based on GC analysis, 1.05 wt % $H_2O_2$ based on titration and 1.73 wt % heavy species by GPC analysis. The DVB conversion was 100% and the $H_2O_2$ conversion was 87.8%. The DVBDO yield was 63% and the DVBMO yield was 0.7%. The total yield of epoxide groups (summed for all three products EVBO, DVBMO, and DVBDO) was 47% based on $H_2O_2$ charged.

The conditions and results of Examples 14 and Comparative Example B are summarized in Table III as follows.

TABLE III

| Example # | PROSTAB 5415 DVB raw material (ppm) | Additional PROSTAB 5415 added[a] (ppm) | $H_2O_2$ conv. (%) | DVB conv. (%) | DVBMO yield based on DVB (%) | DVBDO yield based on DVB (%) | Epoxide yield based on $H_2O_2$ (%) |
|---|---|---|---|---|---|---|---|
| 14 | 1500 | 15944 | 92.1 | 99.9 | 2 | 85 | 64 |
| Comp. Ex. B | 1500 | 0 | 87.8 | 100.0 | 1 | 63 | 47 |

[a] Total PROSTAB 5415 added during reaction in ppm (weight) based on weight of DVB raw material.

The process of the present invention is not to be limited by the specific examples set forth above including the tables to which they refer. Rather, these examples and the tables they refer to are illustrative of the process of the present invention.

What is claimed is:

1. A process for preparing a divinylarene dioxide comprising (I) reacting a mixture of: (a) at least one divinylarene, (b) at least one peroxycarboximidic acid epoxidizing agent, (c) at least one solvent, (d) at least one basic compound, and (e) at least one free radical polymerization inhibitor under conditions to form a divinylarene dioxide product; wherein the mole ratio of peroxycarboximidic acid to the ethylenic double bonds of the divinylarene is less than about 2.0; and wherein the percent yield of divinylarene dioxide product based on divinylarene is greater than about 50 percent.

2. The process of claim 1, wherein the percent yield of divinylarene monoxide based on divinylarene is less than about 50 percent.

3. The process of claim 1, wherein the peroxycarboximidic acid is selected from the group consisting essentially of (i) a pre-formed peroxycarboximidic acid formed separately from the reaction mixture;
(ii) peroxycarboximidic acid formed in situ in the reaction mixture; and (iii) a combination of (i) and (ii).

4. The process of claim 1, including forming the peroxycarboximidic acid in situ in the reaction mixture by adding (i) an aqueous hydrogen peroxide and (ii) a nitrile to the reaction mixture.

5. The process of claim 1, wherein the at least one basic compound is added to the reaction mixture continuously or intermittently during the reaction period or wherein the at least one basic compound is added all at once to the initial reaction sufficient to maintain the pH of the reaction mixture in the range of from about 7 to about 12.

6. The process of claim 1, wherein the divinylarene is divinylbenzene; and wherein the divinylarene dioxide formed is divinylbenzene dioxide.

7. The process of claim 1, wherein the reaction mixture includes an oxygen-containing gas.

8. The process of claim 1, wherein the process includes the steps of:
(II) separating/recovering a divinylarene dioxide product from the other components of the reaction effluent from step (I); and
(III) purifying the divinylarene dioxide product.

9. The process of claim 8, wherein step (III) is a distillation step to obtain a divinylarene dioxide product with greater than about 80 percent purity.

10. The process of claim 8, wherein step (III) includes purifying a divinylarene monoxide, an alkyl-vinyl-arene monoxide, or mixtures thereof.

11. The process of claim 10, wherein the purifying step is a distillation process to provide a divinylarene monoxide or an alkyl-vinyl-arene monoxide with a purity of greater than about 50 percent.

12. The process of claim 8, wherein the process includes the step of:
(IV) converting an amide by-product present in step (II) to a nitrile.

13. The process of claim 12, wherein the process includes the step of:
(V) recycling the nitrile of step (IV) to the reaction step (I).

14. The process of claim 8, wherein step (II) is an extraction/water washing step.

15. The process of claim 8, wherein step (II) is a solvent removal step.

16. The process of claim 8, wherein step (II) includes (i) diluting the reaction effluent with water; (ii) extracting the diluted reaction effluent of step (i) with an extraction solvent; (iii) water washing an organic extract of step (ii) to remove one or more of residual acetamide, residual hydrogen peroxide, and residual basic compound; (iv) distilling the water washed organic extract of step (iii) to remove the extraction solvent; and (v) recovering divinylarene dioxide product.

17. The process of claim 8, wherein step (II) includes recovering the reaction solvent and excess nitrile after the reaction; and recycling the recovered reaction solvent and nitrile.

18. The process of claim 8, wherein step (II) includes distilling the reaction solvent and excess nitrile from the reaction effluent forming a concentrate containing the divinylarene dioxide product; wherein the concentrate separates into two phases; followed by phase separation.

19. The process of claim 1, wherein the free radical polymerization inhibitor is added to the reaction mixture intermittently or continuously over the course of the reaction.

20. The process of claim 1, wherein the inhibitor prevents the divinylarene reactant from polymerizing to form undesired products such that the percent yield of divinylarene dioxide product based on divinylarene is greater than about 50 percent.

* * * * *